United States Patent [19]

Cheever et al.

[11] Patent Number: 5,869,445
[45] Date of Patent: Feb. 9, 1999

[54] METHODS FOR ELICITING OR ENHANCING REACTIVITY TO HER-2/NEU PROTEIN

[75] Inventors: Martin A. Cheever, Mercer Island; Mary L. Disis, Renton, both of Wash.

[73] Assignee: University of Washington, Seattle, Wash.

[21] Appl. No.: 625,101

[22] Filed: Apr. 1, 1996

Related U.S. Application Data

[63] Continuation-in-part of Ser. No. 414,417, Mar. 31, 1995, which is a continuation-in-part of Ser. No. 106,112, Aug. 12, 1993, abandoned, which is a continuation-in-part of Ser. No. 33,644, Mar. 17, 1993, abandoned.

[51] Int. Cl.$^6$ .................................................. A61K 38/17
[52] U.S. Cl. .................................................. 514/2; 514/21
[58] Field of Search .......................... 424/132.1; 514/2, 514/21

[56] References Cited

U.S. PATENT DOCUMENTS

| | | | |
|---|---|---|---|
| 3,766,162 | 10/1973 | Spector | 260/112 R |
| 3,791,932 | 2/1974 | Schuurs et al. | 195/103.5 R |
| 3,817,837 | 6/1974 | Rubenstein et al. | 195/103.5 R |
| 3,850,752 | 11/1974 | Schuurs et al. | 195/103.5 R |
| 3,901,654 | 8/1975 | Gross | 23/230 B |
| 3,935,074 | 1/1976 | Rubenstein et al. | 195/103.5 R |
| 3,984,533 | 10/1976 | Uzgiris | 424/12 |
| 3,996,345 | 12/1976 | Ullman et al. | 424/12 |
| 4,034,074 | 7/1977 | Miles | 424/1 |
| 4,098,876 | 7/1978 | Piasio et al. | 424/1 |
| 4,233,402 | 11/1980 | Maggio et al. | 435/7 |
| 4,452,901 | 6/1984 | Gordon et al. | 436/506 |
| 5,320,947 | 6/1994 | Cheever et al. | 435/29 |
| 5,401,638 | 3/1995 | Carney et al. | 435/7.23 |

FOREIGN PATENT DOCUMENTS

| | | |
|---|---|---|
| WO 90/14357 | 11/1990 | WIPO . |
| WO 91/02062 | 2/1991 | WIPO . |

OTHER PUBLICATIONS

Fisk et al., "Oligopeptide Induction of a Cytotoxic T Lymphocyte Response to HER–2/Neu Proto–oncogene in Vitro," *Cellular Immunology* 157:415–427, 1994.

Ioannides et al., "Cytotoxic T–Cell Clones Isolated from Ovarian Tumour Infiltrating Lymphocytes Recognize Common Determinants on Non–Ovarian Tumour Clones," *Scand. J. Immunol.* 37: 413–424, 1993.

Alper et al., "The Presence of c–erbB–2 Gene Product–related Protein in Culture Medium Conditioned by Breast Cancer Cell Line SK–BR–3," *Cell Growth & Differentiation* 1:591–599, 1990.

Bargmann et al., "The neu oncogene encodes an epidermal growth factor receptor–related protein," *Nature* 319:226–230, 1986.

Baselga et al., "Phase II Study of Weekly Intravenous Recombinant Humanized Anti–p185$^{HER2}$ Monoclonal Antibody in Patients With HER2/neu–Overexpressing Metastatic Breast Cancer," *Journal of Clinical Oncology* 14(3): 737–744, 1996.

Ben–Mahrez et al., "Circulating Antibodies Against C–myc Oncogene Product In Sera Of Colorectal Cancer Patients," *Int. J. Cancer* 46: 35–38, 1990.

Ben–Mahrez et al., "Detection of circulating antibodies against c–myc protein in cancer patient sera," *Br. J. Cancer* 57: 529–534, 1988.

Bishop and Orosz, "Limiting Dilution Analysis For Alloreactive, TCGF–Secretory T Cells. Two Related LDA Methods That Discriminate Between Unstimulated Precursor T Cells and In Vivo–Alloactivated T Cells," *Transplantation* 47(4): 671–677, 1989.

Bodmer, W., "T–Cell Immune Responses to Cancer—A New Look," *Human Immunology* 30:259–261, 1991.

Bowen–Pope et al., "Production of platelet–derived growth factor–like molecules and reduce expression of platelet–derived growth factor receptors accompany transformation by a wide spectrum of agents," *Proc. Natl. Acad. Sci. USA* 81: 2396–2400, 1984.

Brooks et al., "Human lymphocyte markers defined by antibodies derived from somatic cell hybrids," *Clin. exp. Immunol.* 39: 477–485, 1980.

Brown et al., "Protein Antigens of Normal and Malignant Human Cells Identified by Immunoprecipitation with Monoclonal Antibodies," *Journal of Biological Chemistry* 255(11): 4980–4983, 1980.

Burnette et al., "Western Blotting: Electropheretic Transfer of Proteins from Sodium Dodecyl Sulfate–Palyacrylamide Gels to Unmodified Nitrocellulose and Radiographic Detection with Antibody and Radioiodinated Protein A," *Analytical Biochemistry* 112: 195–203, 1981.

Coussens et al., "Tyrosine Kinase Receptor with Extensive Homology to EGF Receptor Shares Chromosomal Location with neu Oncogene," *Science* 230: 1132–1139, 1985.

Dhut et al, "BCR–ABL and BCR Proteins: Biochemical Characterization and Localization," *Leukemia* 4(11): 745–750, 1990.

Disis et al., "Existent T–Cell and Antibody Immunity to HER–2/neu Protein in Patients With Breast Cancer," *Cancer Res.* 54: 16–20, 1994.

Falk et al., "Allele–specific motifs revealed by sequencing of self–peptides eluted from MHC molecules," *Nature* 351: 290–296, 1991.

Feller and de la Cruz, "Identifying antigenic T–cell sites," *Nature* 349: 720–721, 1991.

(List continued on next page.)

*Primary Examiner*—Toni R. Scheiner
*Assistant Examiner*—Nancy A. Johnson
*Attorney, Agent, or Firm*—Seed and Berry LLP

[57] ABSTRACT

Compounds and compositions for eliciting or enhancing immune reactivity to HER-2/neu protein are disclosed. The compounds include polypeptides and nucleic acid molecules encoding such peptides. The compounds may be used for the prevention or treatment of malignancies in which the HER-2/neu oncogene is associated.

4 Claims, 4 Drawing Sheets

OTHER PUBLICATIONS

Flanagan and Leder, "neu protooncogene fused to an immunoglobulin heavy chain gene requires immunoglobulin light chain for cell surface expression and oncogenic transformation," *Proc. Natl. Acad. Sci. USA* 85: 8057–8061, 1998.

Iglehart et al., "Increased erbB–2 Gene Copies and Expression in Multiple Stages of Breast Cancer," *Cancer Research* 50: 6701–6707, 1990.

Ioannides et al., "Antigens Recognized by T cells in Ovarian Cancer," in Abstacts of the Fourth International Conference of Anticancer Research, 21–25 Oct. 1992, Rethymnon, Crete, Greece, p. 1870.

Ioannides et al., "CTL Clones Isolated from Ovarian Tumor Infiltrating Lymphocytes can Recognize Peptides with Sequences Corresponding to the HER2/neu Gene Product," *FASEB Journal* 6: A1404, Abstract No. 2711, 1992.

Ioannides et al., "T–Cell Recognition of Oncogene Products: A New Strategy for Immunotherapy," *Molecular Carcinogenesis* 6: 77–82, 1992.

Ioannides, C.G., "Antigens and vaccines of female genital cancers (Meeting abstract)," Cancerlit Database Abstract No. ICDB/93690682, 1992.

Ioannides et al., "Cytotoxic T Cells Isolated From Ovarian Malignant Ascites Recognize a Peptide Derived From the HER–2/neu Proto–oncogene," *Cell. Immunol.* 151: 225–234, 1993.

Kallioniemi et al., "ERBB2 amplification in breast cancer analyzed by fluorescence in situ hybridization," *Proc. Natl. Acad. Sci.* 89: 5321–5325, 1992.

Kerns et al., "c–erbB–2 Expression In Breast Cancer Detected by Immunoblotting and Immunohistochemistry," *Journal of Histochemistry and Cytochemistry* 38(12): 1823–1830, 1990.

Laemmli, U., "Cleavage of Structural Proteins during the Assembly of the Head of Bacteriophage T4," *Nature* 227: 680–685, 1970.

Leitzel et al., "Elevated Soluble c–erbB2 Antigen Levels in the Serum and Effusions of a Proportion of Breast Cancer Patients," *Journal of Clinical Oncology* 10(9): 1436–1443, 1992.

Lichtenstein et al., "Effects of β–2 Microglobulin Antisense oligonucleotides on Sensitivity of HER2/neu Oncogene–Expressing and Nonexpressing Target Cells to Lymphocyte–Mediated Lysis," *Cellular Immunology* 141: 219–232, 1992.

Lippman, M., "Potential Contributions of Breast Cancer Biology to Management of Breast Cancer", *Advances in Oncology* 8(3): 26–28, 1992.

Maguire and Greene, "The neu (c–erbB–2) Oncogene," *Seminars in Oncology* 16(2): 148–155, 1989.

Margalit et al., "Prediction Of Immunodominant Helper T Cell Antigenic Sites From The Primary Sequence," *Journal of Immunology* 138(7): 2213–2229, 1987.

McGlynn et al., "Large–scale purification and characterisation of a recombinant epidermal growth–factor receptor protein–tyrosine kinase. Modulation of activity by multiple factors," *Eur. J. Biochem.* 207: 265–275, 1992.

McKenzie et al., "Induction of Antitumor Immunity by Immunization with a Vaccinia Virus Vector Expressing and Oncogene–encoded Product," in *Vaccines 88*, Cold Spring Harbor Laboratory, 1988, pp. 19–23.

Mietzner et al., "Purification and Characterization of the Major Iron–Regulated Protein Expressed By Pathogenic Neisseriae," *Journal of Experimental Medicine* 165: 1041–1057, 1987.

Mori et al., "In vitro and in vivo Release of Soluble erbB–2 Protein from Humnan Carcinoma Cells," *Japanese Journal of Cancer Research* 81: 489–494, 1990.

Paik et al., "Pathologic Findings From the National Surgical Adjuvant Breast and Bowel Project: Prognostic Significance of erbB–2 Protein Overexpression in Primary Breast Cancer," *Journal of Clinical Oncology* 8(1): 103–112, 1990.

Parker et al., "Sequence Motifs Important For Peptide Binding To The Human MHC Class I Molecule, HLA–A2," *Journal of Immunology* 149(11): 3580–3587, 1992.

Press et al., "Expression of the HER–2/neu proto–oncogene in normal human adult and fetal tissues," *Oncogene* 5: 953–962, 1990.

Raines and Ross, "Platelet–derived Growth Factor. I. High Yields Purification and Evidence for Multiple Forms," *Journal of Biological Chemistry* 257(9): 5154–5159, 1982.

Riberdy and Cresswell, "The Antigen–Processing Mutant T2 Suggests a Role for MHC–Linked Genes in Class II Antigen Presentation," *Journal of Immunology* 148(8):2586–2590, 1992.

Rothbard and Taylor, "A sequence pattern common to T cell epitopes," *EMBO Journal* 7(1) 93–100, 1988.

Semba et al., "A v–erbB–related protooncogene, c–erbB–2, is distinct from the c–erbB–1/epidermal growth factor–receptor gene and is amplified in a human salivary gland adenocarcinoma," *Proc. Natl. Acad. Sci. USA* 82: 6497–6501, 1985.

Spies et al., "A gene in the human major histocompatibility complex class II region controlling the class I angtigen presentation pathway," *Nature* 348: 744–747, 1990.

Stern et al., "Oncogenic Activation of p185$^{neu}$ Stimulates Tyrosine Phosphorylation In Vivo," *Molecular and Cellular Biology* 8(9): 3969–3973, 1988.

Trowsdale et al., "Sequence encoded in the class II region of the MHC related to the 'ABC' superfamily of transporters," *Nature* 348: 741–744, 1990.

Weiner et al., "A point mutation in the neu oncogene mimics ligand induction of receptor aggregation," *Nature* 339: 230–231, 1989.

Wide, L., "Solid Phase Antigen–Antibody Systems," in *Radioimmunoassay Methods*, Kirkham and Hunter (eds.), 1973, pp. 405–412.

Wisdom, G.B., "Enzyme–Immunoassay," *Clin. Chem.* 22(8): 1243–1255, 1976.

Yamamoto et al., "Similarity of protein encoded by the c–erb–B–2 gene to epidermal growth factor receptor," *Nature* 319: 230–234, 1986.

Zabrecky et al., "The Extracellular Domain of p185/neu Is Released from the Surface of Human Breast Carcinoma Cells, SK–BR–3," *Journal of Biological Chemistry* 266(3): 1716–1720, 1991.

5,869,445

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 3768 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..3765

( x i ) SEQUENCE DESCRIPTION: SEQ ID NO:1:

```
ATG  GAG  CTG  GCG  GCC  TTG  TGC  CGC  TGG  GGG  CTC  CTC  CTC  GCC  CTC  TTG         48
Met  Glu  Leu  Ala  Ala  Leu  Cys  Arg  Trp  Gly  Leu  Leu  Leu  Ala  Leu  Leu
 1              5                        10                       15

CCC  CCC  GGA  GCC  GCG  AGC  ACC  CAA  GTG  TGC  ACC  GGC  ACA  GAC  ATG  AAG         96
Pro  Pro  Gly  Ala  Ala  Ser  Thr  Gln  Val  Cys  Thr  Gly  Thr  Asp  Met  Lys
                 20                       25                       30

CTG  CGG  CTC  CCT  GCC  AGT  CCC  GAG  ACC  CAC  CTG  GAC  ATG  CTC  CGC  CAC        144
Leu  Arg  Leu  Pro  Ala  Ser  Pro  Glu  Thr  His  Leu  Asp  Met  Leu  Arg  His
           35                       40                       45

CTC  TAC  CAG  GGC  TGC  CAG  GTG  GTG  CAG  GGA  AAC  CTG  GAA  CTC  ACC  TAC        192
Leu  Tyr  Gln  Gly  Cys  Gln  Val  Val  Gln  Gly  Asn  Leu  Glu  Leu  Thr  Tyr
      50                       55                       60

CTG  CCC  ACC  AAT  GCC  AGC  CTG  TCC  TTC  CTG  CAG  GAT  ATC  CAG  GAG  GTG        240
Leu  Pro  Thr  Asn  Ala  Ser  Leu  Ser  Phe  Leu  Gln  Asp  Ile  Gln  Glu  Val
 65                       70                       75                       80

CAG  GGC  TAC  GTG  CTC  ATC  GCT  CAC  AAC  CAA  GTG  AGG  CAG  GTC  CCA  CTG        288
Gln  Gly  Tyr  Val  Leu  Ile  Ala  His  Asn  Gln  Val  Arg  Gln  Val  Pro  Leu
                            85                       90                       95
```

| | | | | | | | | | | | | | | | | |
|---|---|---|---|---|---|---|---|---|---|---|---|---|---|---|---|---|
|CAG|AGG|CTG|CGG|ATT|GTG|CGA|GGC|ACC|CAG|CTC|TTT|GAG|GAC|AAC|TAT|336|
|Gln|Arg|Leu|Arg|Ile|Val|Arg|Gly|Thr|Gln|Leu|Phe|Glu|Asp|Asn|Tyr||
| | |100| | | |105| | | |110| | | | | | |
|GCC|CTG|GCC|GTG|CTA|GAC|AAT|GGA|GAC|CCG|CTG|AAC|AAT|ACC|ACC|CCT|384|
|Ala|Leu|Ala|Val|Leu|Asp|Asn|Gly|Asp|Pro|Leu|Asn|Asn|Thr|Thr|Pro||
| | |115| | | |120| | | |125| | | | | | |
|GTC|ACA|GGG|GCC|TCC|CCA|GGA|GGC|CTG|CGG|GAG|CTG|CAG|CTT|CGA|AGC|432|
|Val|Thr|Gly|Ala|Ser|Pro|Gly|Gly|Leu|Arg|Glu|Leu|Gln|Leu|Arg|Ser||
| | |130| | | |135| | | |140| | | | | | |
|CTC|ACA|GAG|ATC|TTG|AAA|GGA|GGG|GTC|TTG|ATC|CAG|CGG|AAC|CCC|CAG|480|
|Leu|Thr|Glu|Ile|Leu|Lys|Gly|Gly|Val|Leu|Ile|Gln|Arg|Asn|Pro|Gln||
| | |145| | | |150| | | |155| | | | |160| |
|CTC|TGC|TAC|CAG|GAC|ACG|ATT|TTG|TGG|AAG|GAC|ATC|TTC|CAC|AAG|AAC|528|
|Leu|Cys|Tyr|Gln|Asp|Thr|Ile|Leu|Trp|Lys|Asp|Ile|Phe|His|Lys|Asn||
| | |165| | | |170| | | |175| | | | | | |
|AAC|CAG|CTG|GCT|CTC|ACA|CTG|ATA|GAC|ACC|AAC|CGC|TCT|CGG|GCC|TGC|576|
|Asn|Gln|Leu|Ala|Leu|Thr|Leu|Ile|Asp|Thr|Asn|Arg|Ser|Arg|Ala|Cys||
| | |180| | | |185| | | |190| | | | | | |
|CAC|CCC|TGT|TCT|CCG|ATG|TGT|AAG|GGC|TCC|CGC|TGC|TGG|GGA|GAG|AGT|624|
|His|Pro|Cys|Ser|Pro|Met|Cys|Lys|Gly|Ser|Arg|Cys|Trp|Gly|Glu|Ser||
| | |195| | | |200| | | |205| | | | | | |
|TCT|GAG|GAT|TGT|CAG|AGC|CTG|ACG|CGC|ACT|GTC|TGT|GCC|GGT|GGC|TGT|672|
|Ser|Glu|Asp|Cys|Gln|Ser|Leu|Thr|Arg|Thr|Val|Cys|Ala|Gly|Gly|Cys||
| |210| | | | |215| | | |220| | | | | | |
|GCC|CGC|TGC|AAG|GGG|CCA|CTG|CCC|ACT|GAC|TGC|TGC|CAT|GAG|CAG|TGT|720|
|Ala|Arg|Cys|Lys|Gly|Pro|Leu|Pro|Thr|Asp|Cys|Cys|His|Glu|Gln|Cys||
|225| | | | |230| | | |235| | | | | |240| |
|GCT|GCC|GGC|TGC|ACG|GGC|CCC|AAG|CAC|TCT|GAC|TGC|CTG|GCC|TGC|CTC|768|
|Ala|Ala|Gly|Cys|Thr|Gly|Pro|Lys|His|Ser|Asp|Cys|Leu|Ala|Cys|Leu||
| | | | |245| | | |250| | | | |255| | |
|CAC|TTC|AAC|CAC|AGT|GGC|ATC|TGT|GAG|CTG|CAC|TGC|CCA|GCC|CTG|GTC|816|
|His|Phe|Asn|His|Ser|Gly|Ile|Cys|Glu|Leu|His|Cys|Pro|Ala|Leu|Val||
| | | |260| | | |265| | | |270| | | | | |
|ACC|TAC|AAC|ACA|GAC|ACG|TTT|GAG|TCC|ATG|CCC|AAT|CCC|GAG|GGC|CGG|864|
|Thr|Tyr|Asn|Thr|Asp|Thr|Phe|Glu|Ser|Met|Pro|Asn|Pro|Glu|Gly|Arg||
| | |275| | | |280| | | |285| | | | | | |
|TAT|ACA|TTC|GGC|GCC|AGC|TGT|GTG|ACT|GCC|TGT|CCC|TAC|AAC|TAC|CTT|912|
|Tyr|Thr|Phe|Gly|Ala|Ser|Cys|Val|Thr|Ala|Cys|Pro|Tyr|Asn|Tyr|Leu||
| |290| | | | |295| | | |300| | | | | | |
|TCT|ACG|GAC|GTG|GGA|TCC|TGC|ACC|CTC|GTC|TGC|CCC|CTG|CAC|AAC|CAA|960|
|Ser|Thr|Asp|Val|Gly|Ser|Cys|Thr|Leu|Val|Cys|Pro|Leu|His|Asn|Gln||
|305| | | | |310| | | |315| | | | | |320| |
|GAG|GTG|ACA|GCA|GAG|GAT|GGA|ACA|CAG|CGG|TGT|GAG|AAG|TGC|AGC|AAG|1008|
|Glu|Val|Thr|Ala|Glu|Asp|Gly|Thr|Gln|Arg|Cys|Glu|Lys|Cys|Ser|Lys||
| | | | |325| | | |330| | | | | |335| | |
|CCC|TGT|GCC|CGA|GTG|TGC|TAT|GGT|CTG|GGC|ATG|GAG|CAC|TTG|CGA|GAG|1056|
|Pro|Cys|Ala|Arg|Val|Cys|Tyr|Gly|Leu|Gly|Met|Glu|His|Leu|Arg|Glu||
| | | |340| | | |345| | | |350| | | | | |
|GTG|AGG|GCA|GTT|ACC|AGT|GCC|AAT|ATC|CAG|GAG|TTT|GCT|GGC|TGC|AAG|1104|
|Val|Arg|Ala|Val|Thr|Ser|Ala|Asn|Ile|Gln|Glu|Phe|Ala|Gly|Cys|Lys||
| | |355| | | |360| | | |365| | | | | | |
|AAG|ATC|TTT|GGG|AGC|CTG|GCA|TTT|CTG|CCG|GAG|AGC|TTT|GAT|GGG|GAC|1152|
|Lys|Ile|Phe|Gly|Ser|Leu|Ala|Phe|Leu|Pro|Glu|Ser|Phe|Asp|Gly|Asp||
| | |370| | | |375| | | |380| | | | | | |
|CCA|GCC|TCC|AAC|ACT|GCC|CCG|CTC|CAG|CCA|GAG|CAG|CTC|CAA|GTG|TTT|1200|
|Pro|Ala|Ser|Asn|Thr|Ala|Pro|Leu|Gln|Pro|Glu|Gln|Leu|Gln|Val|Phe||
|385| | | | |390| | | |395| | | | | |400| |
|GAG|ACT|CTG|GAA|GAG|ATC|ACA|GGT|TAC|CTA|TAC|ATC|TCA|GCA|TGG|CCG|1248|
|Glu|Thr|Leu|Glu|Glu|Ile|Thr|Gly|Tyr|Leu|Tyr|Ile|Ser|Ala|Trp|Pro||
| | | | |405| | | |410| | | | |415| | | |

| | | | | | | | | | | | | | | | | |
|---|---|---|---|---|---|---|---|---|---|---|---|---|---|---|---|---|
| GAC | AGC | CTG | CCT | GAC | CTC | AGC | GTC | TTC | CAG | AAC | CTG | CAA | GTA | ATC | CGG | 1296 |
| Asp | Ser | Leu | Pro 420 | Asp | Leu | Ser | Val | Phe 425 | Gln | Asn | Leu | Gln | Val 430 | Ile | Arg | |
| GGA | CGA | ATT | CTG | CAC | AAT | GGC | GCC | TAC | TCG | CTG | ACC | CTG | CAA | GGG | CTG | 1344 |
| Gly | Arg | Ile 435 | Leu | His | Asn | Gly | Ala 440 | Tyr | Ser | Leu | Thr | Leu 445 | Gln | Gly | Leu | |
| GGC | ATC | AGC | TGG | CTG | GGG | CTG | CGC | TCA | CTG | AGG | GAA | CTG | GGC | AGT | GGA | 1392 |
| Gly | Ile | Ser 450 | Trp | Leu | Gly | Leu | Arg 455 | Ser | Leu | Arg | Glu | Leu 460 | Gly | Ser | Gly | |
| CTG | GCC | CTC | ATC | CAC | CAT | AAC | ACC | CAC | CTC | TGC | TTC | GTG | CAC | ACG | GTG | 1440 |
| Leu | Ala | Leu 465 | Ile | His | His | Asn | Thr 470 | His | Leu | Cys | Phe | Val 475 | His | Thr | Val 480 | |
| CCC | TGG | GAC | CAG | CTC | TTT | CGG | AAC | CCG | CAC | CAA | GCT | CTG | CTC | CAC | ACT | 1488 |
| Pro | Trp | Asp | Gln | Leu 485 | Phe | Arg | Asn | Pro | His 490 | Gln | Ala | Leu | Leu | His 495 | Thr | |
| GCC | AAC | CGG | CCA | GAG | GAC | GAG | TGT | GTG | GGC | GAG | GGC | CTG | GCC | TGC | CAC | 1536 |
| Ala | Asn | Arg | Pro 500 | Glu | Asp | Glu | Cys | Val 505 | Gly | Glu | Gly | Leu | Ala 510 | Cys | His | |
| CAG | CTG | TGC | GCC | CGA | GGG | CAC | TGC | TGG | GGT | CCA | GGG | CCC | ACC | CAG | TGT | 1584 |
| Gln | Leu | Cys 515 | Ala | Arg | Gly | His | Cys 520 | Trp | Gly | Pro | Gly | Pro 525 | Thr | Gln | Cys | |
| GTC | AAC | TGC | AGC | CAG | TTC | CTT | CGG | GGC | CAG | GAG | TGC | GTG | GAG | GAA | TGC | 1632 |
| Val | Asn | Cys 530 | Ser | Gln | Phe | Leu | Arg 535 | Gly | Gln | Glu | Cys | Val 540 | Glu | Glu | Cys | |
| CGA | GTA | CTG | CAG | GGG | CTC | CCC | AGG | GAG | TAT | GTG | AAT | GCC | AGG | CAC | TGT | 1680 |
| Arg 545 | Val | Leu | Gln | Gly | Leu 550 | Pro | Arg | Glu | Tyr | Val 555 | Asn | Ala | Arg | His | Cys 560 | |
| TTG | CCG | TGC | CAC | CCT | GAG | TGT | CAG | CCC | CAG | AAT | GGC | TCA | GTG | ACC | TGT | 1728 |
| Leu | Pro | Cys | His | Pro 565 | Glu | Cys | Gln | Pro | Gln 570 | Asn | Gly | Ser | Val | Thr 575 | Cys | |
| TTT | GGA | CCG | GAG | GCT | GAC | CAG | TGT | GTG | GCC | TGT | GCC | CAC | TAT | AAG | GAC | 1776 |
| Phe | Gly | Pro | Glu 580 | Ala | Asp | Gln | Cys | Val 585 | Ala | Cys | Ala | His | Tyr 590 | Lys | Asp | |
| CCT | CCC | TTC | TGC | GTG | GCC | CGC | TGC | CCC | AGC | GGT | GTG | AAA | CCT | GAC | CTC | 1824 |
| Pro | Pro | Phe 595 | Cys | Val | Ala | Arg | Cys 600 | Pro | Ser | Gly | Val | Lys 605 | Pro | Asp | Leu | |
| TCC | TAC | ATG | CCC | ATC | TGG | AAG | TTT | CCA | GAT | GAG | GAG | GGC | GCA | TGC | CAG | 1872 |
| Ser | Tyr | Met | Pro | Ile 610 | Trp | Lys | Phe | Pro | Asp 615 | Glu | Glu | Gly | Ala 620 | Cys | Gln | |
| CCT | TGC | CCC | ATC | AAC | TGC | ACC | CAC | TCC | TGT | GTG | GAC | CTG | GAT | GAC | AAG | 1920 |
| Pro 625 | Cys | Pro | Ile | Asn | Cys 630 | Thr | His | Ser | Cys | Val 635 | Asp | Leu | Asp | Asp | Lys 640 | |
| GGC | TGC | CCC | GCC | GAG | CAG | AGA | GCC | AGC | CCT | CTG | ACG | TCC | ATC | ATC | TCT | 1968 |
| Gly | Cys | Pro | Ala | Glu 645 | Gln | Arg | Ala | Ser | Pro 650 | Leu | Thr | Ser | Ile | Ile 655 | Ser | |
| GCG | GTG | GTT | GGC | ATT | CTG | CTG | GTC | GTG | GTC | TTG | GGG | GTG | GTC | TTT | GGG | 2016 |
| Ala | Val | Val | Gly | Ile 660 | Leu | Leu | Val | Val | Val 665 | Leu | Gly | Val | Val | Phe 670 | Gly | |
| ATC | CTC | ATC | AAG | CGA | CGG | CAG | CAG | AAG | ATC | CGG | AAG | TAC | ACG | ATG | CGG | 2064 |
| Ile | Leu | Ile 675 | Lys | Arg | Arg | Gln | Gln 680 | Lys | Ile | Arg | Lys | Tyr 685 | Thr | Met | Arg | |
| AGA | CTG | CTG | CAG | GAA | ACG | GAG | CTG | GTG | GAG | CCG | CTG | ACA | CCT | AGC | GGA | 2112 |
| Arg | Leu | Leu 690 | Gln | Glu | Thr | Glu | Leu 695 | Val | Glu | Pro | Leu | Thr 700 | Pro | Ser | Gly | |
| GCG | ATG | CCC | AAC | CAG | GCG | CAG | ATG | CGG | ATC | CTG | AAA | GAG | ACG | GAG | CTG | 2160 |
| Ala | Met | Pro | Asn | Gln 705 | Ala | Gln | Met | Arg | Ile 710 | Leu | Lys | Glu | Thr 715 | Glu | Leu 720 | |
| AGG | AAG | GTG | AAG | GTG | CTT | GGA | TCT | GGC | GCT | TTT | GGC | ACA | GTC | TAC | AAG | 2208 |
| Arg | Lys | Val | Lys | Val 725 | Leu | Gly | Ser | Gly | Ala 730 | Phe | Gly | Thr | Val | Tyr 735 | Lys | |

| | | | | | | | | | | | | | | | | |
|---|---|---|---|---|---|---|---|---|---|---|---|---|---|---|---|---|
| GGC | ATC | TGG | ATC | CCT | GAT | GGG | GAG | AAT | GTG | AAA | ATT | CCA | GTG | GCC | ATC | 2256 |
| Gly | Ile | Trp | Ile 740 | Pro | Asp | Gly | Glu | Asn 745 | Val | Lys | Ile | Pro 750 | Val | Ala | Ile | |
| AAA | GTG | TTG | AGG | GAA | AAC | ACA | TCC | CCC | AAA | GCC | AAC | AAA | GAA | ATC | TTA | 2304 |
| Lys | Val | Leu 755 | Arg | Glu | Asn | Thr | Ser 760 | Pro | Lys | Ala | Asn 765 | Lys | Glu | Ile | Leu | |
| GAC | GAA | GCA | TAC | GTG | ATG | GCT | GGT | GTG | GGC | TCC | CCA | TAT | GTC | TCC | CGC | 2352 |
| Asp | Glu 770 | Ala | Tyr | Val | Met 775 | Ala | Gly | Val | Gly | Ser 780 | Pro | Tyr | Val | Ser | Arg | |
| CTT | CTG | GGC | ATC | TGC | CTG | ACA | TCC | ACG | GTG | CAG | CTG | GTG | ACA | CAG | CTT | 2400 |
| Leu | Leu 785 | Gly | Ile | Cys | Leu 790 | Thr | Ser | Thr | Val 795 | Gln | Leu | Val | Thr | Gln | Leu 800 | |
| ATG | CCC | TAT | GGC | TGC | CTC | TTA | GAC | CAT | GTC | CGG | GAA | AAC | CGC | GGA | CGC | 2448 |
| Met | Pro | Tyr | Gly | Cys 805 | Leu | Leu | Asp | His | Val 810 | Arg | Glu | Asn | Arg | Gly 815 | Arg | |
| CTG | GGC | TCC | CAG | GAC | CTG | CTG | AAC | TGG | TGT | ATG | CAG | ATT | GCC | AAG | GGG | 2496 |
| Leu | Gly | Ser | Gln 820 | Asp | Leu | Leu | Asn | Trp 825 | Cys | Met | Gln | Ile | Ala 830 | Lys | Gly | |
| ATG | AGC | TAC | CTG | GAG | GAT | GTG | CGG | CTC | GTA | CAC | AGG | GAC | TTG | GCC | GCT | 2544 |
| Met | Ser | Tyr 835 | Leu | Glu | Asp | Val | Arg 840 | Leu | Val | His | Arg | Asp 845 | Leu | Ala | Ala | |
| CGG | AAC | GTG | CTG | GTC | AAG | AGT | CCC | AAC | CAT | GTC | AAA | ATT | ACA | GAC | TTC | 2592 |
| Arg | Asn 850 | Val | Leu | Val | Lys | Ser 855 | Pro | Asn | His | Val | Lys 860 | Ile | Thr | Asp | Phe | |
| GGG | CTG | GCT | CGG | CTG | CTG | GAC | ATT | GAC | GAG | ACA | GAG | TAC | CAT | GCA | GAT | 2640 |
| Gly | Leu | Ala | Arg 865 | Leu | Leu | Asp | Ile 870 | Asp | Glu | Thr | Glu 875 | Tyr | His | Ala | Asp 880 | |
| GGG | GGC | AAG | GTG | CCC | ATC | AAG | TGG | ATG | GCG | CTG | GAG | TCC | ATT | CTC | CGC | 2688 |
| Gly | Gly | Lys | Val | Pro 885 | Ile | Lys | Trp | Met | Ala 890 | Leu | Glu | Ser | Ile | Leu 895 | Arg | |
| CGG | CGG | TTC | ACC | CAC | CAG | AGT | GAT | GTG | TGG | AGT | TAT | GGT | GTG | ACT | GTG | 2736 |
| Arg | Arg | Phe | Thr 900 | His | Gln | Ser | Asp | Val 905 | Trp | Ser | Tyr | Gly | Val 910 | Thr | Val | |
| TGG | GAG | CTG | ATG | ACT | TTT | GGG | GCC | AAA | CCT | TAC | GAT | GGG | ATC | CCA | GCC | 2784 |
| Trp | Glu | Leu | Met 915 | Thr | Phe | Gly | Ala | Lys 920 | Pro | Tyr | Asp | Gly | Ile 925 | Pro | Ala | |
| CGG | GAG | ATC | CCT | GAC | CTG | CTG | GAA | AAG | GGG | GAG | CGG | CTG | CCC | CAG | CCC | 2832 |
| Arg | Glu | Ile | Pro 930 | Asp | Leu | Leu | Glu | Lys 935 | Gly | Glu | Arg | Leu | Pro 940 | Gln | Pro | |
| CCC | ATC | TGC | ACC | ATT | GAT | GTC | TAC | ATG | ATC | ATG | GTC | AAA | TGT | TGG | ATG | 2880 |
| Pro | Ile | Cys | Thr | Ile 950 | Asp | Val | Tyr | Met | Ile 955 | Met | Val | Lys | Cys | Trp 960 | Met | |
| ATT | GAC | TCT | GAA | TGT | CGG | CCA | AGA | TTC | CGG | GAG | TTG | GTG | TCT | GAA | TTC | 2928 |
| Ile | Asp | Ser | Glu | Cys 965 | Arg | Pro | Arg | Phe | Arg 970 | Glu | Leu | Val | Ser | Glu 975 | Phe | |
| TCC | CGC | ATG | GCC | AGG | GAC | CCC | CAG | CGC | TTT | GTG | GTC | ATC | CAG | AAT | GAG | 2976 |
| Ser | Arg | Met | Ala | Arg 980 | Asp | Pro | Gln | Arg | Phe 985 | Val | Val | Ile | Gln | Asn 990 | Glu | |
| GAC | TTG | GGC | CCA | GCC | AGT | CCC | TTG | GAC | AGC | ACC | TTC | TAC | CGC | TCA | CTG | 3024 |
| Asp | Leu | Gly | Pro 995 | Ala | Ser | Pro | Leu | Asp 1000 | Ser | Thr | Phe | Tyr | Arg 1005 | Ser | Leu | |
| CTG | GAG | GAC | GAT | GAC | ATG | GGG | GAC | CTG | GTG | GAT | GCT | GAG | GAG | TAT | CTG | 3072 |
| Leu | Glu | Asp | Asp 1010 | Asp | Met | Gly | Asp | Leu 1015 | Val | Asp | Ala | Glu | Glu 1020 | Tyr | Leu | |
| GTA | CCC | CAG | CAG | GGC | TTC | TTC | TGT | CCA | GAC | CCT | GCC | CCG | GGC | GCT | GGG | 3120 |
| Val | Pro | Gln | Gln | Gly 1030 | Phe | Phe | Cys | Pro | Asp 1035 | Pro | Ala | Pro | Gly | Ala 1040 | Gly | |
| | | | | 1025 | | | | | | | | | | | | |
| GGC | ATG | GTC | CAC | CAC | AGG | CAC | CGC | AGC | TCA | TCT | ACC | AGG | AGT | GGC | GGT | 3168 |
| Gly | Met | Val | His | His 1045 | Arg | His | Arg | Ser | Ser 1050 | Ser | Thr | Arg | Ser | Gly 1055 | Gly | |

| | | | | | | | | | | | | | | | | |
|---|---|---|---|---|---|---|---|---|---|---|---|---|---|---|---|---|
| GGG | GAC | CTG | ACA | CTA | GGG | CTG | GAG | CCC | TCT | GAA | GAG | GAG | GCC | CCC | AGG | 3216 |
| Gly | Asp | Leu | Thr | Leu | Gly | Leu | Glu | Pro | Ser | Glu | Glu | Glu | Ala | Pro | Arg | |
| | | | 1060 | | | | | 1065 | | | | | 1070 | | | |
| TCT | CCA | CTG | GCA | CCC | TCC | GAA | GGG | GCT | GGC | TCC | GAT | GTA | TTT | GAT | GGT | 3264 |
| Ser | Pro | Leu | Ala | Pro | Ser | Glu | Gly | Ala | Gly | Ser | Asp | Val | Phe | Asp | Gly | |
| | | | 1075 | | | | | 1080 | | | | | 1085 | | | |
| GAC | CTG | GGA | ATG | GGG | GCA | GCC | AAG | GGG | CTG | CAA | AGC | CTC | CCC | ACA | CAT | 3312 |
| Asp | Leu | Gly | Met | Gly | Ala | Ala | Lys | Gly | Leu | Gln | Ser | Leu | Pro | Thr | His | |
| | | 1090 | | | | | 1095 | | | | | 1100 | | | | |
| GAC | CCC | AGC | CCT | CTA | CAG | CGG | TAC | AGT | GAG | GAC | CCC | ACA | GTA | CCC | CTG | 3360 |
| Asp | Pro | Ser | Pro | Leu | Gln | Arg | Tyr | Ser | Glu | Asp | Pro | Thr | Val | Pro | Leu | |
| 1105 | | | | | 1110 | | | | | 1115 | | | | | 1120 | |
| CCC | TCT | GAG | ACT | GAT | GGC | TAC | GTT | GCC | CCC | CTG | ACC | TGC | AGC | CCC | CAG | 3408 |
| Pro | Ser | Glu | Thr | Asp | Gly | Tyr | Val | Ala | Pro | Leu | Thr | Cys | Ser | Pro | Gln | |
| | | | | 1125 | | | | | 1130 | | | | | 1135 | | |
| CCT | GAA | TAT | GTG | AAC | CAG | CCA | GAT | GTT | CGG | CCC | CAG | CCC | CCT | TCG | CCC | 3456 |
| Pro | Glu | Tyr | Val | Asn | Gln | Pro | Asp | Val | Arg | Pro | Gln | Pro | Pro | Ser | Pro | |
| | | | 1140 | | | | | 1145 | | | | | 1150 | | | |
| CGA | GAG | GGC | CCT | CTG | CCT | GCT | GCC | CGA | CCT | GCT | GGT | GCC | ACT | CTG | GAA | 3504 |
| Arg | Glu | Gly | Pro | Leu | Pro | Ala | Ala | Arg | Pro | Ala | Gly | Ala | Thr | Leu | Glu | |
| | | | 1155 | | | | | 1160 | | | | | 1165 | | | |
| AGG | CCC | AAG | ACT | CTC | TCC | CCA | GGG | AAG | AAT | GGG | GTC | GTC | AAA | GAC | GTT | 3552 |
| Arg | Pro | Lys | Thr | Leu | Ser | Pro | Gly | Lys | Asn | Gly | Val | Val | Lys | Asp | Val | |
| | | 1170 | | | | | 1175 | | | | | 1180 | | | | |
| TTT | GCC | TTT | GGG | GGT | GCC | GTG | GAG | AAC | CCC | GAG | TAC | TTG | ACA | CCC | CAG | 3600 |
| Phe | Ala | Phe | Gly | Gly | Ala | Val | Glu | Asn | Pro | Glu | Tyr | Leu | Thr | Pro | Gln | |
| 1185 | | | | | 1190 | | | | | 1195 | | | | | 1200 | |
| GGA | GGA | GCT | GCC | CCT | CAG | CCC | CAC | CCT | CCT | CCT | GCC | TTC | AGC | CCA | GCC | 3648 |
| Gly | Gly | Ala | Ala | Pro | Gln | Pro | His | Pro | Pro | Pro | Ala | Phe | Ser | Pro | Ala | |
| | | | | 1205 | | | | | 1210 | | | | | 1215 | | |
| TTC | GAC | AAC | CTC | TAT | TAC | TGG | GAC | CAG | GAC | CCA | CCA | GAG | CGG | GGG | GCT | 3696 |
| Phe | Asp | Asn | Leu | Tyr | Tyr | Trp | Asp | Gln | Asp | Pro | Pro | Glu | Arg | Gly | Ala | |
| | | | 1220 | | | | | 1225 | | | | | 1230 | | | |
| CCA | CCC | AGC | ACC | TTC | AAA | GGG | ACA | CCT | ACG | GCA | GAG | AAC | CCA | GAG | TAC | 3744 |
| Pro | Pro | Ser | Thr | Phe | Lys | Gly | Thr | Pro | Thr | Ala | Glu | Asn | Pro | Glu | Tyr | |
| | | | 1235 | | | | | 1240 | | | | | 1245 | | | |
| CTG | GGT | CTG | GAC | GTG | CCA | GTG | TGA | | | | | | | | | 3768 |
| Leu | Gly | Leu | Asp | Val | Pro | Val | | | | | | | | | | |
| | | 1250 | | | | | 1255 | | | | | | | | | |

( 2 ) INFORMATION FOR SEQ ID NO:2:

( i ) SEQUENCE CHARACTERISTICS:
        ( A ) LENGTH: 1255 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Glu | Leu | Ala | Ala | Leu | Cys | Arg | Trp | Gly | Leu | Leu | Leu | Ala | Leu | Leu |
| 1 | | | | 5 | | | | | 10 | | | | | 15 | |
| Pro | Pro | Gly | Ala | Ala | Ser | Thr | Gln | Val | Cys | Thr | Gly | Thr | Asp | Met | Lys |
| | | | 20 | | | | | 25 | | | | | 30 | | |
| Leu | Arg | Leu | Pro | Ala | Ser | Pro | Glu | Thr | His | Leu | Asp | Met | Leu | Arg | His |
| | | 35 | | | | | 40 | | | | | 45 | | | |
| Leu | Tyr | Gln | Gly | Cys | Gln | Val | Val | Gln | Gly | Asn | Leu | Glu | Leu | Thr | Tyr |
| | 50 | | | | | 55 | | | | | 60 | | | | |
| Leu | Pro | Thr | Asn | Ala | Ser | Leu | Ser | Phe | Leu | Gln | Asp | Ile | Gln | Glu | Val |
| 65 | | | | | 70 | | | | | 75 | | | | | 80 |

| | | | | | | | | | | | | | | |
|---|---|---|---|---|---|---|---|---|---|---|---|---|---|---|
|Gln|Gly|Tyr|Val|Leu 85|Ile|Ala|His|Asn|Gln 90|Val|Arg|Gln|Val|Pro 95|Leu|
|Gln|Arg|Leu|Arg 100|Ile|Val|Arg|Gly|Thr 105|Gln|Leu|Phe|Glu|Asp 110|Asn|Tyr|
|Ala|Leu|Ala 115|Val|Leu|Asp|Asn|Gly 120|Asp|Pro|Leu|Asn|Asn 125|Thr|Thr|Pro|
|Val|Thr 130|Gly|Ala|Ser|Pro|Gly 135|Gly|Leu|Arg|Glu|Leu 140|Gln|Leu|Arg|Ser|
|Leu 145|Thr|Glu|Ile|Leu|Lys 150|Gly|Gly|Val|Leu|Ile 155|Gln|Arg|Asn|Pro|Gln 160|
|Leu|Cys|Tyr|Gln|Asp 165|Thr|Ile|Leu|Trp|Lys 170|Asp|Ile|Phe|His|Lys 175|Asn|
|Asn|Gln|Leu|Ala 180|Leu|Thr|Leu|Ile|Asp 185|Thr|Asn|Arg|Ser|Arg 190|Ala|Cys|
|His|Pro|Cys 195|Ser|Pro|Met|Cys|Lys 200|Gly|Ser|Arg|Cys|Trp 205|Gly|Glu|Ser|
|Ser|Glu 210|Asp|Cys|Gln|Ser|Leu 215|Thr|Arg|Thr|Val|Cys 220|Ala|Gly|Gly|Cys|
|Ala 225|Arg|Cys|Lys|Gly|Pro 230|Leu|Pro|Thr|Asp|Cys 235|Cys|His|Glu|Gln|Cys 240|
|Ala|Ala|Gly|Cys|Thr 245|Gly|Pro|Lys|His|Ser 250|Asp|Cys|Leu|Ala|Cys 255|Leu|
|His|Phe|Asn|His 260|Ser|Gly|Ile|Cys|Glu 265|Leu|His|Cys|Pro|Ala 270|Leu|Val|
|Thr|Tyr|Asn 275|Thr|Asp|Thr|Phe|Glu 280|Ser|Met|Pro|Asn|Pro 285|Glu|Gly|Arg|
|Tyr|Thr 290|Phe|Gly|Ala|Ser|Cys 295|Val|Thr|Ala|Cys|Pro 300|Tyr|Asn|Tyr|Leu|
|Ser|Thr 305|Asp|Val|Gly|Ser 310|Cys|Thr|Leu|Val|Cys 315|Pro|Leu|His|Asn|Gln 320|
|Glu|Val|Thr|Ala|Glu 325|Asp|Gly|Thr|Gln|Arg 330|Cys|Glu|Lys|Cys|Ser 335|Lys|
|Pro|Cys|Ala|Arg 340|Val|Cys|Tyr|Gly|Leu 345|Gly|Met|Glu|His|Leu 350|Arg|Glu|
|Val|Arg|Ala 355|Val|Thr|Ser|Ala|Asn 360|Ile|Gln|Glu|Phe|Ala 365|Gly|Cys|Lys|
|Lys|Ile 370|Phe|Gly|Ser|Leu|Ala 375|Phe|Leu|Pro|Glu|Ser 380|Phe|Asp|Gly|Asp|
|Pro 385|Ala|Ser|Asn|Thr|Ala 390|Pro|Leu|Gln|Pro|Glu 395|Gln|Leu|Gln|Val|Phe 400|
|Glu|Thr|Leu|Glu|Glu 405|Ile|Thr|Gly|Tyr|Leu 410|Tyr|Ile|Ser|Ala|Trp 415|Pro|
|Asp|Ser|Leu|Pro 420|Asp|Leu|Ser|Val|Phe 425|Gln|Asn|Leu|Gln|Val 430|Ile|Arg|
|Gly|Arg|Ile 435|Leu|His|Asn|Gly|Ala 440|Tyr|Ser|Leu|Thr|Leu 445|Gln|Gly|Leu|
|Gly|Ile 450|Ser|Trp|Leu|Gly|Leu 455|Arg|Ser|Leu|Arg|Glu 460|Leu|Gly|Ser|Gly|
|Leu 465|Ala|Leu|Ile|His|His 470|Asn|Thr|His|Leu|Cys 475|Phe|Val|His|Thr|Val 480|
|Pro|Trp|Asp|Gln|Leu 485|Phe|Arg|Asn|Pro|His 490|Gln|Ala|Leu|Leu|His 495|Thr|
|Ala|Asn|Arg|Pro 500|Glu|Asp|Glu|Cys|Val 505|Gly|Glu|Gly|Leu|Ala 510|Cys|His|

```
Gln  Leu  Cys  Ala  Arg  Gly  His  Cys  Trp  Gly  Pro  Gly  Pro  Thr  Gln  Cys
          515                520                     525

Val  Asn  Cys  Ser  Gln  Phe  Leu  Arg  Gly  Gln  Glu  Cys  Val  Glu  Glu  Cys
     530                535                     540

Arg  Val  Leu  Gln  Gly  Leu  Pro  Arg  Glu  Tyr  Val  Asn  Ala  Arg  His  Cys
545                550                     555                          560

Leu  Pro  Cys  His  Pro  Glu  Cys  Gln  Pro  Gln  Asn  Gly  Ser  Val  Thr  Cys
               565                     570                          575

Phe  Gly  Pro  Glu  Ala  Asp  Gln  Cys  Val  Ala  Cys  Ala  His  Tyr  Lys  Asp
               580                585                     590

Pro  Pro  Phe  Cys  Val  Ala  Arg  Cys  Pro  Ser  Gly  Val  Lys  Pro  Asp  Leu
               595                600                     605

Ser  Tyr  Met  Pro  Ile  Trp  Lys  Phe  Pro  Asp  Glu  Glu  Gly  Ala  Cys  Gln
          610                615                     620

Pro  Cys  Pro  Ile  Asn  Cys  Thr  His  Ser  Cys  Val  Asp  Leu  Asp  Asp  Lys
625                     630                     635                          640

Gly  Cys  Pro  Ala  Glu  Gln  Arg  Ala  Ser  Pro  Leu  Thr  Ser  Ile  Ile  Ser
                    645                     650                     655

Ala  Val  Val  Gly  Ile  Leu  Leu  Val  Val  Leu  Gly  Val  Val  Phe  Gly
                    660                     665                     670

Ile  Leu  Ile  Lys  Arg  Arg  Gln  Gln  Lys  Ile  Arg  Lys  Tyr  Thr  Met  Arg
          675                     680                     685

Arg  Leu  Leu  Gln  Glu  Thr  Glu  Leu  Val  Glu  Pro  Leu  Thr  Pro  Ser  Gly
     690                     695                     700

Ala  Met  Pro  Asn  Gln  Ala  Gln  Met  Arg  Ile  Leu  Lys  Glu  Thr  Glu  Leu
705                     710                     715                          720

Arg  Lys  Val  Lys  Val  Leu  Gly  Ser  Gly  Ala  Phe  Gly  Thr  Val  Tyr  Lys
                    725                     730                          735

Gly  Ile  Trp  Ile  Pro  Asp  Gly  Glu  Asn  Val  Lys  Ile  Pro  Val  Ala  Ile
               740                     745                     750

Lys  Val  Leu  Arg  Glu  Asn  Thr  Ser  Pro  Lys  Ala  Asn  Lys  Glu  Ile  Leu
          755                     760                     765

Asp  Glu  Ala  Tyr  Val  Met  Ala  Gly  Val  Gly  Ser  Pro  Tyr  Val  Ser  Arg
     770                     775                     780

Leu  Leu  Gly  Ile  Cys  Leu  Thr  Ser  Thr  Val  Gln  Leu  Val  Thr  Gln  Leu
785                     790                     795                          800

Met  Pro  Tyr  Gly  Cys  Leu  Leu  Asp  His  Val  Arg  Glu  Asn  Arg  Gly  Arg
                    805                     810                     815

Leu  Gly  Ser  Gln  Asp  Leu  Leu  Asn  Trp  Cys  Met  Gln  Ile  Ala  Lys  Gly
               820                     825                     830

Met  Ser  Tyr  Leu  Glu  Asp  Val  Arg  Leu  Val  His  Arg  Asp  Leu  Ala  Ala
               835                     840                     845

Arg  Asn  Val  Leu  Val  Lys  Ser  Pro  Asn  His  Val  Lys  Ile  Thr  Asp  Phe
     850                     855                     860

Gly  Leu  Ala  Arg  Leu  Leu  Asp  Ile  Asp  Glu  Thr  Glu  Tyr  His  Ala  Asp
865                     870                     875                          880

Gly  Gly  Lys  Val  Pro  Ile  Lys  Trp  Met  Ala  Leu  Glu  Ser  Ile  Leu  Arg
                    885                     890                     895

Arg  Arg  Phe  Thr  His  Gln  Ser  Asp  Val  Trp  Ser  Tyr  Gly  Val  Thr  Val
               900                     905                     910

Trp  Glu  Leu  Met  Thr  Phe  Gly  Ala  Lys  Pro  Tyr  Asp  Gly  Ile  Pro  Ala
          915                     920                     925
```

```
Arg Glu Ile Pro Asp Leu Leu Glu Lys Gly Glu Arg Leu Pro Gln Pro
        930             935                 940

Pro Ile Cys Thr Ile Asp Val Tyr Met Ile Met Val Lys Cys Trp Met
945             950                 955                     960

Ile Asp Ser Glu Cys Arg Pro Arg Phe Arg Glu Leu Val Ser Glu Phe
                965             970                 975

Ser Arg Met Ala Arg Asp Pro Gln Arg Phe Val Val Ile Gln Asn Glu
            980             985                 990

Asp Leu Gly Pro Ala Ser Pro Leu Asp Ser Thr Phe Tyr Arg Ser Leu
        995             1000                1005

Leu Glu Asp Asp Asp Met Gly Asp Leu Val Asp Ala Glu Glu Tyr Leu
        1010            1015                1020

Val Pro Gln Gln Gly Phe Phe Cys Pro Asp Pro Ala Pro Gly Ala Gly
1025            1030            1035                    1040

Gly Met Val His His Arg His Arg Ser Ser Thr Arg Ser Gly Gly
                1045            1050                1055

Gly Asp Leu Thr Leu Gly Leu Glu Pro Ser Glu Glu Glu Ala Pro Arg
            1060            1065            1070

Ser Pro Leu Ala Pro Ser Glu Gly Ala Gly Ser Asp Val Phe Asp Gly
        1075            1080            1085

Asp Leu Gly Met Gly Ala Ala Lys Gly Leu Gln Ser Leu Pro Thr His
    1090            1095            1100

Asp Pro Ser Pro Leu Gln Arg Tyr Ser Glu Asp Pro Thr Val Pro Leu
1105            1110            1115                    1120

Pro Ser Glu Thr Asp Gly Tyr Val Ala Pro Leu Thr Cys Ser Pro Gln
            1125            1130                1135

Pro Glu Tyr Val Asn Gln Pro Asp Val Arg Pro Gln Pro Pro Ser Pro
        1140                1145                1150

Arg Glu Gly Pro Leu Pro Ala Ala Arg Pro Ala Gly Ala Thr Leu Glu
            1155            1160            1165

Arg Pro Lys Thr Leu Ser Pro Gly Lys Asn Gly Val Val Lys Asp Val
        1170            1175            1180

Phe Ala Phe Gly Gly Ala Val Glu Asn Pro Glu Tyr Leu Thr Pro Gln
1185            1190            1195                    1200

Gly Gly Ala Ala Pro Gln Pro His Pro Pro Pro Ala Phe Ser Pro Ala
            1205            1210                1215

Phe Asp Asn Leu Tyr Tyr Trp Asp Gln Asp Pro Pro Glu Arg Gly Ala
            1220            1225                1230

Pro Pro Ser Thr Phe Lys Gly Thr Pro Thr Ala Glu Asn Pro Glu Tyr
        1235            1240                1245

Leu Gly Leu Asp Val Pro Val
        1250            1255
```

( 2 ) INFORMATION FOR SEQ ID NO:3:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
TCTGGCGCGC TGGATGACGA TGACAAGAAA CGACGGCAGC AGAAGATC                48
```

( 2 ) INFORMATION FOR SEQ ID NO:4:

( i ) SEQUENCE CHARACTERISTICS:

(A) LENGTH: 39 base pairs
(B) TYPE: nucleic acid
(C) STRANDEDNESS: single
(D) TOPOLOGY: linear (xi) SEQUENCE DESCRIPTION: SEQ ID NO:4:

TGAATTCTCG AGTCATTACA CTGGCACGTC CAGACCCAG 39

METHODS FOR ELICITING OR ENHANCING REACTIVITY TO HER-2/NEU PROTEIN

CROSS REFERENCE TO RELATED APPLICATION

This application is a continuation-in-part to Ser. No. 414,417, filed Mar. 31, 1995, which is a continuation-in-part application to Ser. No. 106,112, filed Aug. 12, 1993, abandoned, which is a continuation-in-part application to Ser. No. 033,644, filed Mar. 17, 1993, abandoned.

TECHNICAL FIELD

The present invention is generally directed toward polypeptides, and nucleic acid molecules encoding such polypeptides, for eliciting or enhancing an immune response to HER-2/neu protein, including for use in the treatment of malignancies in which the HER-2/neu oncogene is associated.

BACKGROUND OF THE INVENTION

Despite enormous investments of financial and human resources, cancer remains one of the major causes of death. For example, cancer is the leading cause of death in women between the ages of 35 and 74. Breast cancer is the most common malignancy in women and the incidence for developing breast cancer is on the rise. One in nine women will be diagnosed with the disease. Standard approaches to cure breast cancer have centered around a combination of surgery, radiation and chemotherapy. These approaches have resulted in some dramatic successes in certain malignancies. However, these approaches have not been successful for all malignancies and breast cancer is most often incurable when attempting to treat beyond a certain stage. Alternative approaches to prevention and therapy are necessary.

A common characteristic of malignancies is uncontrolled cell growth. Cancer cells appear to have undergone a process of transformation from the normal phenotype to a malignant phenotype capable of autonomous growth. Amplification and overexpression of somatic cell genes is considered to be a common primary event that results in the transformation of normal cells to malignant cells. The malignant phenotypic characteristics encoded by the oncogenic genes are passed on during cell division to the progeny of the transformed cells.

Ongoing research involving oncogenes has identified at least forty oncogenes operative in malignant cells and responsible for, or associated with, transformation. Oncogenes have been classified into different groups based on the putative function or location of their gene products (such as the protein expressed by the oncogene).

Oncogenes are believed to be essential for certain aspects of normal cellular physiology. In this regard, the HER-2/neu oncogene is a member of the tyrosine protein kinase family of oncogenes and shares a high degree of homology with the epidermal growth factor receptor. HER-2/neu presumably plays a role in cell growth and/or differentiation. HER-2/neu appears to induce malignancies through quantitative mechanisms that result from increased or deregulated expression of an essentially normal gene product.

HER-2/neu (p185) is the protein product of the HER-2/neu oncogene. The HER-2/neu gene is amplified and the HER-2/neu protein is overexpressed in a variety of cancers including breast, ovarian, colon, lung and prostate cancer. HER-2/neu is related to malignant transformation. It is found in 50%–60% of ductal in situ carcinoma and 20%–40% of all breast cancers, as well as a substantial fraction of adenocarcinomas arising in the ovaries, prostate, colon and lung. HER-2/neu is intimately associated not only with the malignant phenotype, but also with the aggressiveness of the malignancy, being found in one-fourth of all invasive breast cancers. HER-2/neu overexpression is correlated with a poor prognosis in both breast and ovarian cancer. HER-2/neu is a transmembrane protein with a relative molecular mass of 185 kd that is approximately 1255 amino acids (aa) in length. It has an extracellular binding domain (ECD) of approximately 645 aa, with 40% homology to epidermal growth factor receptor (EGFR), a highly hydrophobic transmembrane anchor domain (TMD), and a carboxyterminal cytoplasmic domain (CD) of approximately 580 aa with 80% homology to EGFR.

Due to the difficulties in the current approaches to therapy of cancers in which the HER-2/neu oncogene is associated, there is a need in the art for improved compounds and compositions. The present invention fulfills this need, and further provides other related advantages.

SUMMARY OF THE INVENTION

Briefly stated, the present invention provides polypeptides, nucleic acid molecules (directing the expression of such polypeptides) and viral vectors (directing the expression of such polypeptides) for uses which include the immunization of a warm-blooded animal against a malignancy in which the HER-2/neu oncogene is associated. A polypeptide or nucleic acid molecule according to this invention may be present in a composition that includes a pharmaceutically acceptable carrier or diluent. Such a polypeptide, nucleic acid molecule, viral vector or pharmaceutical composition may be administered on a one-time basis (e.g., when a malignancy is suspected) or on a periodic basis (e.g., for an individual with an elevated risk of acquiring or reacquiring a malignancy). A compound or composition of the present invention may be useful in the treatment of an existing tumor or to prevent tumor occurrence or reoccurrence.

In one aspect, the present invention provides compounds and compositions that elicit or enhance an immune response to HER-2/neu protein. One embodiment of the present invention provides a polypeptide encoded by a DNA sequence selected from: (a) nucleotides 2026 through 3765 of SEQ ID NO:1; and (b) DNA sequences that hybridize to a nucleotide sequence complementary to nucleotides 2026 through 3765 of SEQ ID NO:1 under moderately stringent conditions, wherein the DNA sequence encodes a polypeptide that produces an immune response to HER-2/neu protein. In a preferred embodiment, a polypeptide has the amino acid sequence of SEQ ID NO:2 from lysine, amino acid 676, through valine, amino acid 1255, or a variant thereof that produces at least an equivalent immune response. A composition is provided that comprises a polypeptide of the present invention in combination with a pharmaceutically acceptable carrier or diluent. In another embodiment, a nucleic acid molecule directing the expression of a polypeptide according to the present invention is provided. In another embodiment, a viral vector directing the expression of a polypeptide according to the present invention is provided.

In another aspect, the present invention provides a method for eliciting or enhancing an immune response to HER-2/neu protein, comprising administering to a warm-blooded animal (such as a human) in an amount effective to elicit or enhance the response a polypeptide according to the present invention, or a nucleic acid molecule or a viral vector, either directing the expression of such a polypeptide. In one embodiment, a peptide is administered in combination with a pharmaceutically acceptable carrier or diluent. In another embodiment, the step of administering comprises transfecting cells of the animal ex vivo with the nucleic acid molecule and subsequently delivering the transfected cells to the animal. In another embodiment, the step of administering comprises infecting cells of the animal ex vivo with the viral vector and subsequently delivering the infected cells to the animal.

These and other aspects of the present invention will become evident upon reference to the following detailed description and attached drawings.

DETAILED DESCRIPTION OF THE INVENTION

Figure 1:
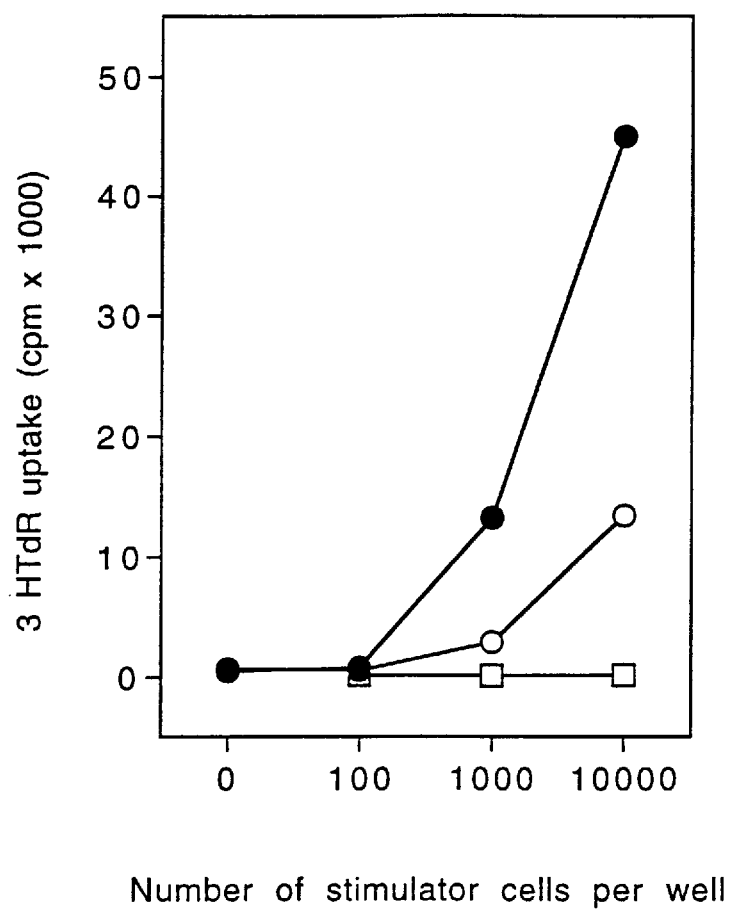
FIG. 1 shows the results of the priming of naive T lymphocytes to HER-2/neu polypeptide by dendritic cells. Bone marrow-derived DC were generated with GM-CSF and IL6 from CD34+ stem cells. DC pulsed with HER-2/neu polypeptide induced protein-specific proliferation of autologous CD4+/CD45RA+ T lymphocytes after 7 days of culturing T cells with DC. Bone marrow-derived CD34+stem cells cultured for one week in serum-free medium containing GM-CSF and IL-6 were used as APC. APC were plated into 96-well round-bottomed plates (Corning, Corning, N.Y., USA) at various concentrations and incubated for 16–18 hours with 20–25 μg/ml of recombinant HER-2/neu polypeptide. CD4+ T lymphocytes were isolated from autologous peripheral blood mononuclear cells by positive selection using immunoaffinity columns (CellPro, Inc., Bothell, Wash., USA). Antigen-pulsed APC were irradiated (10 Gy), and CD4+ T lymphocytes were added at $10^5$ per well. Proliferative response of T cells was measured by the uptake of ($^3$H)thymidine (1μCi/well) added on day 7 for 1618 hours. Proliferation assays were performed in serum- and cytokine-free medium in 5 well replicates. The symbols represent: ● DC+HER-2/neu polypeptide+CD4+/CD45RA+ T cells; ○ DC+CD4+/CD45RA+ T cells; and □ DC+HER-2/neu polypeptide.

Prior to setting forth the invention, it may be helpful to an understanding thereof to set forth definitions of certain terms to be used hereinafter.

HER-2/neu polypeptide-as used herein, refers to a portion of the HER-2/neu protein (the protein also known as p185 or c-erbB2) having the amino acid sequence of SEQ ID NO:2 from lysine, amino acid 676, through valine, amino acid 1255; and may be naturally derived, synthetically produced, genetically engineered, or a functionally equivalent variant thereof, e.g., where one or more amino acids are replaced by other amino acid(s) or non-amino acid(s) which do not substantially affect elicitation or enhancement of an immune response to HER2/neu protein (e.g., variant stimulates a response by helper T cells or cytotoxic T cells).

Proliferation of T cells-as used herein, includes the multiplication of T cells as well as the stimulation of T cells leading to multiplication, i.e., the initiation of events leading to mitosis and mitosis itself. Methods for detecting proliferation of T cells are discussed below.

As noted above, the present invention is directed toward compounds and compositions to elicit or enhance immunity to the protein product expressed by the HER-2/neu oncogene, including for malignancies in a warm-blooded animal wherein an amplified HER-2/neu gene is associated with the malignancies. Association of an amplified HER-2/neu gene with a malignancy does not require that the protein expression product of the gene be present on the tumor. For example, overexpression of the protein expression product may be involved with initiation of a tumor, but the protein expression may subsequently be lost. A use of the present invention is to elicit or enhance an effective autochthonous immune response to convert a HER-2/neu positive tumor to HER-2/neu negative.

More specifically, the disclosure of the present invention, in one aspect, shows that a polypeptide based on a particular portion (HER-2/neu polypeptide) of the protein expression product of the HER-2/neu gene can be recognized by thymus-dependent lymphocytes (hereinafter "T cells") and, therefore, the autochthoncus immune T cell response can be utilized prophylactically or to treat malignancies in which such a protein is or has been overexpressed. The disclosure of the present invention also shows, in another aspect, that nucleic acid molecules directing the expression of such a peptide may be used alone or in a viral vector for immunization.

In general, CD4+ T cell populations are considered to function as helpers/inducers through the release of lymphokines when stimulated by a specific antigen; however, a subset of CD4$^+$ cells can act as cytotoxic T lymphocytes (CTL). Similarly, CD8$^+$ T cells are considered to function by directly lysing antigenic targets; however, under a variety of circumstances they can secrete lymphokines to provide helper or DTH function. Despite the potential of overlapping function, the phenotypic CD4 and CD8 markers are linked to the recognition of peptides bound to class II or class I MHC antigens. The recognition of antigen in the context of class II or class I MHC mandates that $CD4^+$ and $CD8^+$ T cells respond to different antigens or the same antigen presented under different circumstances. The binding of immunogenic peptides to class II MHC antigens most commonly occurs for antigens ingested by antigen presenting cells. Therefore, $CD4^+$ T cells generally recognize antigens that have been external to the tumor cells. By contrast, under normal circumstances, binding of peptides to class I MHC occurs only for proteins present in the cytosol and synthesized by the target itself, proteins in the external environment are excluded. An exception to this is the binding of exogenous peptides with a precise class I binding motif which are present outside the cell in high concentration. Thus, $CD4^+$ and $CD8^+$ T cells have broadly different functions and tend to recognize different antigens as a reflection of where the antigens normally reside.

As disclosed within the present invention, a polypeptide portion of the protein product expressed by the HER-2/neu oncogene is recognized by T cells. Circulating HER-2/neu polypeptide is degraded to peptide fragments. Peptide fragments from the polypeptide bind to major histocompatibility complex (MHC) antigens. By display of a peptide bound to MHC antigen on the cell surface and recognition by host T cells of the combination of peptide plus self MHC antigen, HER-2/neu polypeptide (including that expressed on a malignant cell) will be immunogenic to T cells. The exquisite specificity of the T cell receptor enables individual T cells to discriminate between peptides which differ by a single amino acid residue.

During the immune response to a peptide fragment from the polypeptide, T cells expressing a T cell receptor with high affinity binding of the peptide-MHC complex will bind to the peptide-MHC complex and thereby become activated and induced to proliferate. In the first encounter with a peptide, small numbers of immune T cells will secrete lymphokines, proliferate and differentiate into effector and memory T cells. The primary immune response will occur in vivo but has been difficult to detect in vitro. Subsequent encounter with the same antigen by the memory T cell will lead to a faster and more intense immune response. The secondary response will occur either in vivo or in vitro. The in vitro response is easily gauged by measuring the degree of proliferation, the degree of cytokine production, or the generation of cytolytic activity of the T cell population re-exposed in the antigen. Substantial proliferation of the T cell population in response to a particular antigen is considered to be indicative of prior exposure or priming to the antigen.

The compounds of this invention generally comprise HER-2/neu polypeptides or DNA molecules that direct the expression of such peptides, wherein the DNA molecules may be present in a viral vector. As noted above, the polypeptides of the present invention include variants of the polypeptide of SEQ ID NO:2 from amino acid 676 through amino acid 1255, that retain the ability to stimulate an immune response. Such variants include various structural forms of the native polypeptide. Due to the presence of ionizable amino and carboxyl groups, for example, a HER-2/neu polypeptide may be in the form of an acidic or basic salt, or may be in neutral form. Individual amino acid residues may also be modified by oxidation or reduction.

Variants within the scope of this invention also include polypeptides in which the primary amino acid structure native HER-2/neu polypeptide is modified by forming covalent or aggregative conjugates with other peptides or polypeptides, or chemical moieties such as glycosyl groups, lipids, phosphate, acetyl groups and the like. Covalent derivatives may be prepared, for example, by linking particular functional groups to amino acid side chains or at the N- or C-terminus.

The present invention also includes HER-2/neu polypeptides with or without glycosylation. Polypeptides expressed in yeast or mammalian expression systems may be similar to or slightly different in molecular weight and glycosylation pattern than the native molecules, depending upon the expression system. For instance, expression of DNA encoding polypeptides in bacteria such as E. coli typically provides non-glycosylated molecules. N-glycosylation sites of eukaryotic proteins are characterized by the amino acid triplet Asn-$A_1$-Z, where $A_1$ is any amino acid except Pro, and Z is Ser or Thr. Variants of HER-2/neu polypeptides having inactivated N-glycosylation sites can be produced by techniques known to those of ordinary skill in the art, such as oligonucleotide synthesis and ligation or site-specific mutagenesis techniques, and are within the scope of this invention. Alternatively, N-linked glycosylation sites can be added to a HER-2/neu polypeptide.

The polypeptides of this invention also include variants of the SEQ ID NO:2 polypeptide (i.e., variants of a polypeptide having the amino acid sequence of SEQ ID NO:2 from amino acid 676 through amino acid 1255) that have an amino acid sequence different from this sequence because of one or more deletions, insertions, substitutions or other modifications. In one embodiment, such variants are substantially homologous to the native HER-2/neu polypeptide and retain the ability to stimulate an immune response. "Substantial homology," as used herein, refers to amino acid sequences that may be encoded by DNA sequences that are capable of hybridizing under moderately stringent conditions to a nucleotide sequence complimentary to a naturally occurring DNA sequence encoding the specified polypeptide portion of SEQ ID NO:2 herein (i.e., nucleotides 2026 through 3765 of SEQ ID NO:1). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2X, 0.5X and 0.2X SSC (containing 0.1% SDS). Such hybridizing DNA sequences are also within the scope of this invention. The effect of any such modifications on the ability of a HER-2/neu polypeptide to produce an immune response may be readily determined (e.g., by analyzing the ability of the mutated HER-2/neu polypeptide to induce a T cell response using, for example, the methods described herein).

Generally, amino acid substitutions may be made in a variety of ways to provide other embodiments of variants within the present invention. First, for example, amino acid substitutions may be made conservatively; i.e., a substitute amino acid replaces an amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. An example of a non-conservative change is to replace an amino acid of one group with an amino acid from another group.

Another way to make amino acid substitutions to produce variants of the present invention is to identify and replace amino acids in T cell motifs with potential to bind to class II MHC molecules (for CD4+ T cell response) or class I MHC molecules (for CD8+ T cell response). Peptide segments (of a HER-2/neu polypeptide) with a motif with theoretical potential to bind to class II MHC molecules may be identified by computer analysis. For example, a protein sequence analysis package, T Sites, that incorporates several computer algorithms designed to distinguish potential sites for T cell recognition can be used (Feller and de la Cruz, Nature 349:720–721, 1991). Two searching algorithms are used: (1) the AMPHI algorithm described by Margalit (Feller and de la Cruz, *Nature* 349:720–721, 1991; Margalit et al., *J. Immunol.* 138:2213–2229, 1987) identifies epitope motifs according to alpha-helical periodicity and amphipathicity; (2) the Rothbard and Taylor algorithm identifies epitope motifs according to charge and polarity pattern (Rothbard and Taylor, EMBO 7:93–100, 1988). Segments with both motifs are most appropriate for binding to class II MHC molecules. CD8+ T cells recognize peptide bound to class I MHC molecules. Falk et al. have determined that peptides binding to particular MHC molecules share discernible sequence motifs (Falk et al., *Nature* 351:290–296, 1991). A peptide motif for binding in the groove of HLA-A2.1 has been defined by Edman degradation of peptides stripped from HLA-A2.1 molecules of a cultured cell line (Table 2, from Falk et al., supra). The method identified the typical or average HLA-A2.1 binding peptide as being 9 amino acids in length with dominant anchor residues occurring at positions 2 (L) and 9 (V). Commonly occurring strong binding residues have been identified at positions 2 (M), 4 (E,K), 6 (V), and 8 (K). The identified motif represents the average of many binding peptides.

The HLA-A2.1 Restricted Motif

| | Amino Acid Position | | | | | | | | | Point Assignment |
|---|---|---|---|---|---|---|---|---|---|---|
| | 1 | 2 | 3 | 4 | 5 | 6 | 7 | 8 | 9 | |
| Dominant Binding Anchor Residue | | L | | | | | | | V | +3 |
| Strong Binding Residue | | M | | E K | | V | | K | | +2 |
| Weak Binding Residue | I L F K M Y | A Y F P M S | G P K D T G V H | I K L Y N | I L T | A Y T H | E Y S | L | | +1 |

The derived peptide motif as currently defined is not particularly stringent. Some HLA-A2.1 binding peptides do not contain both dominant anchor residues and the amino acids flanking the dominant anchor residues play major roles in allowing or disallowing binding. Not every peptide with the current described binding motif will bind, and some peptides without the motif will bind. However, the current motif is valid enough to allow identification of some peptides capable of binding. Of note, the current HLA-A2.1 motif places 6 amino acids between the dominant anchor amino acids at residues 2 and 9.

Following identification of peptide motifs within a HER-2/neu polypeptide, amino acid substitutions may be made conservatively or non-conservatively. The latter type of substitutions are intended to produce an improved polypeptide that is more potent and/or more broadly cross-reactive (MHC polymorphism). An example of a more potent polypeptide is one that binds with higher affinity to the same MHC molecule as natural polypeptide, without affecting recognition by T cells specific for natural polypeptide. An example of a polypeptide with broader cross-reactivity is one that induces more broadly cross-reactive immune responses (i.e., binds to a greater range of MHC molecules) than natural polypeptide. Similarly, one or more amino acids residing between peptide motifs and having a spacer function (e.g., do not interact with a MHC molecule or T cell receptor) may be substituted conservatively or non-conservatively. It will be evident to those of ordinary skill in the art that polypeptides containing one or more amino acid substitutions may be tested for beneficial or adverse immunological interactions by a variety of assays, including those described herein for the ability to stimulate T cell recognition.

Variants within the scope of this invention may also, or alternatively, contain other modifications, including the deletion or addition of amino acids, that have minimal influence on the desired immunological properties of the polypeptide. It will be appreciated by those of ordinary skill in the art that truncated forms or non-native extended forms of a HER-2/neu polypeptide may be used, provided the desired immunological properties are at least roughly equivalent to that of full length, native HER-2/neu polypeptide. Cysteine residues may be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present.

A HER-2/neu polypeptide may generally be obtained using a genomic or cDNA clone encoding the protein. A genomic sequence that encodes full length HER-2/neu is shown in SEQ ID NO:1, and the deduced amino acid sequence is presented in SEQ ID NO:2. Such clones may be isolated by screening an appropriate expression library for clones that express HER-2/neu protein. The library preparation and screen may generally be performed using methods known to those of ordinary skill in the art, such as methods described in Sambrook et al., *Molecular Cloning: A Laboratory Manual*, Cold Spring Harbor Laboratories, Cold Spring Harbor, N.Y., 1989, which is incorporated herein by reference. Briefly, a bacteriophage expression library may be plated and transferred to filters. The filters may then be incubated with a detection reagent. In the context of this invention, a "detection reagent" is any compound capable of binding to HER-2/neu protein, which may then be detected by any of a variety of means known to those of ordinary skill in the art. Typical detection reagents contain a "binding agent," such as Protein A, Protein G, IgG or a lectin, coupled to a reporter group. Preferred reporter groups include enzymes, substrates, cofactors, inhibitors, dyes, radionuclides, luminescent groups, fluorescent groups and biotin. More preferably, the reporter group is horseradish peroxidase, which may be detected by incubation with a substrate such as tetramethylbenzidine or 2,2'-azino-di-3-ethylbenz-thiazoline sulfonic acid. Plaques containing genomic or cDNA sequences that express HER-2/neu protein are isolated and purified by techniques known to those of ordinary skill in the art. Appropriate methods may be found, for example, in Sambrook et al., *Molecular Cloning: A Laboratory Manual*, Cold Spring Harbor Laboratories, Cold Spring Harbor, N.Y., 1989.

Variants of the polypeptide that retain the ability to stimulate an immune response may generally be identified by modifying the sequence in one or more of the aspects described above and assaying the resulting polypeptide for the ability to stimulate an immune response, e.g., a T cell response. For example, such assays may generally be performed by contacting T cells with the modified polypeptide and assaying the response. Naturally occurring variants of the polypeptide may also be isolated by, for example, screening an appropriate cDNA or genomic library with a DNA sequence encoding the polypeptide or a variant thereof.

The above-described sequence modifications may be introduced using standard recombinant techniques or by automated synthesis of the modified polypeptide. For example, mutations can be introduced at particular loci by synthesizing oligonucleotides containing a mutant sequence, flanked by restriction sites enabling ligation to fragments of the native sequence. Following ligation, the resulting reconstructed sequence encodes an analogue having the desired amino acid insertion, substitution, or deletion.

Alternatively, oligonucleotide-directed site-specific mutagenesis procedures can be employed to provide a gene in which particular codons are altered according to the substitution, deletion, or insertion required.

Exemplary methods of making the alterations set forth above are disclosed by Walder et al., Gene 42:133, 1986; Bauer et al., Gene 37:73, 1985; Craik, BioTechniques, Jan. 1985, 12–19; Smith et al., Genetic Engineering: Principles and Methods, Plenum Press, 1981; and U.S. Pat. Nos. 4,518,584 and 4,737,462.

Mutations in nucleotide sequences constructed for expression of such HER-2/neu polypeptides must, of course, preserve the reading frame of the coding sequences and preferably will not create complementary regions that could hybridize to produce secondary mRNA structures, such as loops or hairpins, which would adversely affect translation of the mRNA. Although a mutation site may be predetermined, it is not necessary that the nature of the mutation per se be predetermined. For example, in order to select for optimum characteristics of mutants at a given site, random mutagenesis may be conducted at the target codon and the expressed HER-2/neu polypeptide mutants screened for the desired activity.

Not all mutations in a nucleotide sequence which encodes a HER-2/neu polypeptide will be expressed in the final product. For example, nucleotide substitutions may be made to enhance expression, primarily to avoid secondary structure loops in the transcribed mRNA (see, e.g., European Patent Application 75,444A), or to provide codons that are more readily translated by the selected host, such as the well-known E. coli preference codons for E. coli expression.

The polypeptides of the present invention, both naturally occurring and modified, are preferably produced by recombinant DNA methods. Such methods include inserting a DNA sequence encoding a HER-2/neu polypeptide into a recombinant expression vector and expressing the DNA sequence in a recombinant microbial, mammalian or insect cell expression system under conditions promoting expression. DNA sequences encoding the polypeptides provided by this invention can be assembled from cDNA fragments and short oligonucleotide linkers, or from a series of oligonucleotides, to provide a synthetic gene which is capable of being inserted in a recombinant expression vector and expressed in a recombinant transcriptional unit.

Recombinant expression vectors contain a DNA sequence encoding a HER-2/neu polypeptide operably linked to suitable transcriptional or translational regulatory elements derived from mammalian, microbial, viral or insect genes. Such regulatory elements include a transcriptional promoter, an optional operator sequence to control transcription, a sequence encoding suitable mRNA ribosomal binding sites, and sequences which control the termination of transcription and translation. An origin of replication and a selectable marker to facilitate recognition of transformants may additionally be incorporated.

DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, in reading frame. DNA sequences encoding HER-2/neu polypeptides which are to be expressed in a microorganism will preferably contain no introns that could prematurely terminate transcription of DNA into mRNA.

Expression vectors for bacterial use may comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. E. coli is typically transformed using derivatives of pBR322, a plasmid derived from an E. coli species (Bolivar et al., Gene 2:95, 1977). pBR322 contains genes for ampicillin and tetracycline resistance and thus provides simple means for identifying transformed cells.

Promoters commonly used in recombinant microbial expression vectors include the β-lactamase (penicillinase) and lactose promoter system (Chang et al., Nature 275:615, 1978; and Goeddel et al., Nature 281:544, 1979), the tryptophan (trp) promoter system (Goeddel et al., Nucl. Acids Res. 8:4057, 1980; and European Patent Application 36,776) and the tac promoter (Maniatis, Molecular Cloning: A Laboratory Manual, Cold Spring Harbor Laboratory, p. 412, 1982). A particularly useful bacterial expression system employs the phage λ $P_L$ promoter and cI857ts thermolabile repressor. Plasmid vectors available from the American Type Culture Collection which incorporate derivatives of the λ $P_L$ promoter include plasmid pHUB2, resident in E. coli strain JMB9 (ATCC 37092) and pPLc28, resident in E. coli RR1 (ATCC 53082).

Suitable promoter sequences in yeast vectors include the promoters for metallothionein, 3-phosphoglycerate kinase (Hitzeman et al., J. Biol. Chem. 255:2073, 1980) or other glycolytic enzymes (Hess et al., J. Adv. Enzyme Reg. 7:149, 1968; and Holland et al., Biochem. 17:4900, 1978), such as enolase, glyceralde-hyde 3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., European Patent Application 73,657.

Preferred yeast vectors can be assembled using DNA sequences from pBR322 for selection and replication in E.

coli (Amp$^r$ gene and origin of replication) and yeast DNA sequences including a glucose-repressible ADH2 promoter and α-factor secretion leader. The ADH2 promoter has been described by Russell et al. (*J. Biol. Chem.* 258:2674, 1982) and Beier et al. (*Nature* 300:724, 1982). The yeast α-factor leader, which directs secretion of heterologous proteins, can be inserted between the promoter and the structural gene to be expressed (see, e.g., Kurjan et al., *Cell* 30:933, 1982; and Bitter et al., *Proc. Natl. Acad. Sci. USA* 81:5330, 1984). The leader sequence may be modified to contain, near its 3' end, one or more useful restriction sites to facilitate fusion of the leader sequence to foreign genes. The transcriptional and translational control sequences in expression vectors to be used in transforming vertebrate cells may be provided by viral sources. For example, commonly used promoters and enhancers are derived from polyoma, adenovirus 2, simian virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978). Smaller or larger SV40 fragments may also be used, provided the approximately 250 bp sequence extending from the Hind III site toward the Bgl II site located in the viral origin of replication is included. Further, viral genomic promoter, control and/or signal sequences may be utilized, provided such control sequences are compatible with the host cell chosen. Exemplary vectors can be constructed as disclosed by Okayama and Berg, *Mol. Cell. Biol.* 3:280, 1983.

A useful system for stable high level expression of mammalian receptor cDNAs in C127 murine mammary epithelial cells can be constructed substantially as described by Cosman et al. (*Mol. Immunol.* 23:935, 1986). A preferred eukaryotic vector for expression of HER-2/neu polypeptide DNA is pDC406 (McMahan et al., *EMBO J.* 10:2821, 1991), and includes regulatory sequences derived from SV40, human immunodeficiency virus (HIV), and Epstein-Barr virus (EBV). Other preferred vectors include pDC409 and pDC410, which are derived from pDC406. pDC410 was derived from pDC406 by substituting the EBV origin of replication with sequences encoding the SV40 large T antigen. pDC409 differs from pDC406 in that a Bgl II restriction site outside of the multiple cloning site has been deleted, making the Bgl II site within the multiple cloning site unique.

A useful cell line that allows for episomal replication of expression vectors, such as pDC406 and pDC409, which contain the EBV origin of replication, is CV-1/EBNA (ATCC CRL 10478). The CV-L/EBNA cell line was derived by transfection of the CV-1 cell line with a gene encoding Epstein-Barr virus nuclear antigen-I (EBNA-1) and constitutively express EBNA-1 driven from human CMV immediate-early enhancer/promoter.

Transformed host cells are cells which have been transformed or transfected with expression vectors constructed using recombinant DNA techniques and which contain sequences encoding a HER-2/neu polypeptide of the present invention. Transformed host cells may express the desired HER-2/neu polypeptide, but host cells transformed for purposes of cloning or amplifying HER-2/neu DNA do not need to express the HER-2/neu polypeptide. Expressed polypeptides will preferably be secreted into the culture supernatant, depending on the DNA selected, but may also be deposited in the cell membrane.

Suitable host cells for expression of recombinant proteins include prokaryotes, yeast or higher eukaryotic cells under the control of appropriate promoters. Prokaryotes include gram negative or gram positive organisms, for example *E. coli* or Bacilli. Higher eukaryotic cells include established cell lines of insect or mammalian origin as described below. Cell-free translation systems could also be employed to produce HER-2/neu polypeptides using RNAs derived from DNA constructs. Appropriate cloning and expression vectors for use with bacterial, fungal, yeast, and mammalian cellular hosts are described, for example, by Pouwels et al., *Cloning Vectors: A Laboratory Manual*, Elsevier, N.Y., 1985.

Prokaryotic expression hosts may be used for expression of HER-2/neu polypeptides that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium,* and various species within the genera Pseudomonas, Streptomyces, and Staphylococcus, although other hosts may also be employed.

Recombinant HER-2/neu polypeptides may also be expressed in yeast hosts, preferably from the Saccharomyces species, such as *S. cerevisiae.* Yeast of other genera, such as Pichia or Kluyveromyces may also be employed. Yeast vectors will generally contain an origin of replication from the 2 μ yeast plasmid or an autonomously replicating sequence (ARS), a promoter, DNA encoding the HER-2/neu polypeptide, sequences for polyadenylation and transcription termination and a selection gene. Preferably, yeast vectors will include an origin of replication and selectable marker permitting transformation of both yeast and *E. coli,* e.g., the ampicillin resistance gene of *E. coli* and the *S. cerevisiae* trp1 gene, which provides a selection marker for a mutant strain of yeast lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable yeast transformation protocols are known to those of skill in the art. An exemplary technique described by Hind et al. (*Proc. Natl. Acad. Sci. USA* 75:1929, 1978), involves selecting for Trp$^+$ transformants in a selective medium consisting of 0.67% yeast nitrogen base, 0.5% casamino acids, 2% glucose, 10 mg/ml adenine and 20 mg/ml uracil. Host strains transformed by vectors comprising the ADH2 promoter may be grown for expression in a rich medium consisting of 1% yeast extract, 2% peptone, and 1% glucose supplemented with 80 mg/ml adenine and 80 mg/ml uracil. Derepression of the ADH2 promoter occurs upon exhaustion of medium glucose. Crude yeast supernatants are harvested by filtration and held at 4° C. prior to further purification.

Various mammalian or insect (e.g., Spodoptera or Trichoplusia) cell culture systems can also be employed to express recombinant polypeptide. Baculovirus systems for production of heterologous polypeptides in insect cells are reviewed, for example, by Luckow and Summers, *Bio/Technology* 6:47, 1988. Examples of suitable mammalian host cell lines include the COS-7 lines of monkey kidney cells, described by Gluzman (*Cell* 23:175, 1981), and other cell lines capable of expressing an appropriate vector including, for example, CV-1/EBNA (ATCC CRL 10478), L cells, C127, 3T3, Chinese hamster ovary (CHO), COS, NS-1, HeLa and BHK cell lines. Mammalian expression vectors may comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

Purified HER-2/neu polypeptides may be prepared by culturing suitable host/vector systems to express the recombinant translation products of the DNAs of the resent invention, which are then purified from culture media or cell extracts. For example, supernatants from systems which secrete recombinant polypeptide into culture media may be first concentrated using a commercially available protein concentration filter, such as an Amicon or Millipore Pellicon ultrafiltration unit. Following the concentration step, the concentrate may be applied to a suitable purification matrix. For example, a suitable affinity matrix may comprise a counter structure protein (i.e., a protein to which a HER-2/neu polypeptide binds in a specific interaction based on structure) or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Gel filtration chromatography also provides a means of purifying a HER-2/neu.

Affinity chromatography is a preferred method of purifying HER-2/neu polypeptides. For example, monoclonal antibodies against the HER-2/neu polypeptide may also be useful in affinity chromatography purification, by utilizing methods that are well-known in the art.

Finally, one or more reverse-phase high performance liquid chromatography (RP-HPLC) steps employing hydrophobic RP-HPLC media (e.g., silica gel having pendant methyl or other aliphatic groups) may be employed to further purify a HER-2/neu polypeptide composition. Some or all of the foregoing purification steps, in various combinations, can also be employed to provide a homogeneous recombinant polypeptide.

Recombinant HER-2/neu polypeptide produced in bacterial culture is preferably isolated by initial extraction from cell pellets, followed by one or more concentration, salting-out, aqueous ion exchange or size exclusion chromatography steps. High performance liquid chromatography (HPLC) may be employed for final purification steps. Microbial cells employed in expression of recombinant HER-2/neu polypeptide can be disrupted by any convenient method, including freeze-thaw cycling, sonication, mechanical disruption, or use of cell lysing agents.

Fermentation of yeast which express HER-2/neu polypeptide as a secreted protein greatly simplifies purification. Secreted recombinant protein resulting from a large-scale fermentation can be purified by methods analogous to those disclosed by Urdal et al. (*J. Chromatog.* 296:171, 1984). This reference describes two sequential, reverse-phase HPLC steps for purification of recombinant human GM-CSF on a preparative HPLC column.

Preparations of HER-2/neu polypeptides synthesized in recombinant culture may contain non-HER-2/neu cell components, including proteins, in amounts and of a character which depend upon the purification steps taken to recover the HER-2/neu polypeptide from the culture. These components ordinarily will be of yeast, prokaryotic or non-human eukaryotic origin. Such preparations are typically free of other proteins which may be normally associated with the HER-2/neu protein as it is found in nature in its species of origin.

Automated synthesis provides an alternate method for preparing polypeptides of this invention. For example, any of the commercially available solid-phase techniques may be employed, such as the Merrifield solid phase synthesis method, in which amino acids are sequentially added to a growing amino acid chain. (See Merrifield, *J. Am. Chem. Soc.* 85:2149–2146, 1963.) Equipment for automated synthesis of polypeptides is commercially available from suppliers such as Applied Biosystems, Inc. of Foster City, Calif., and may generally be operated according to the manufacturer's instructions.

Within one aspect of the present invention, use of a HER-2/neu polypeptide (or a DNA molecule that directs the expression of such a peptide) to generate an immune response to the HER-2/neu protein (including that expressed on a malignancy in which a HER-2/neu oncogene is associated) may be detected. Representative examples of such malignancies include breast, ovarian, colon, lung and prostate cancers. An immune response to the HER-2/neu protein, once generated by a HER-2/neu polypeptide, can be long-lived and can be detected long after immunization, regardless of whether the protein is present or absent in the body at the time of testing. An immune response to the HER-2/neu protein generated by reaction to a HER-2/neu polypeptide can be detected by examining for the presence or absence, or enhancement, of specific activation of $CD4^+$ or $CD8^+$ T cells. More specifically, T cells isolated from an immunized individual by routine techniques (such as by Ficoll/Hypaque density gradient centrifugation of peripheral blood lymphocytes) are incubated with HER-2/neu protein. For example, T cells may be incubated in vitro for 2–9 days (typically 4 days) at 37° C. with HER-2/neu protein (typically, 5 μg/ml of whole protein or graded numbers of cells synthesizing HER-2/neu protein). It may be desirable to incubate another aliquot of a T cell sample in the absence of HER-2/neu protein to serve as a control.

Specific activation of $CD4^+$ or $CD8^+$ T cells may be detected in a variety of ways. Methods for detecting specific T cell activation include detecting the proliferation of T cells, the production of cytokines (e.g., lymphokines), or the generation of cytolytic activity (i.e., generation of cytotoxic T cells specific for HER-2/neu protein). For $CD4^+$ T cells, a preferred method for detecting specific T cell activation is the detection of the proliferation of T cells. For $CD8^+$ T cells, a preferred method for detecting specific T cell activation is the detection of the generation of cytolytic activity.

Detection of the proliferation of T cells may be accomplished by a variety of known techniques. For example, T cell proliferation can be detected by measuring the rate of DNA synthesis. T cells which have been stimulated to proliferate exhibit an increased rate of DNA synthesis. A typical way to measure the rate of DNA synthesis is, for example, by pulse-labeling cultures of T cells with tritiated thymidine, a nucleoside precursor which is incorporated into newly synthesized DNA. The amount of tritiated thymidine incorporated can be determined using a liquid scintillation spectrophotometer. Other ways to detect T cell proliferation include measuring increases in interleukin-2 (IL-2) production, $Ca^{2+}$ flux, or dye uptake, such as 3-(4,5-dimethylthiazol-2yl)-2,5-diphenyl-tetrazolium. Alternatively, synthesis of lymphokines (such as interferon-gamma) can be measured or the relative number of T cells that can respond to intact $p185^{HER-2/neu}$ protein may be quantified.

By use or expression of a HER-2/neu polypeptide, T cells which recognize the HER-2/neu protein can be proliferated in vivo. For example, immunization with a HER-2/neu peptide (i.e., as a vaccine) can induce continued expansion in the number of T cells necessary for therapeutic attack against a tumor in which the HER-2/neu oncogene is associated. Typically, about 0.01 μg/kg to about 100 mg/kg body weight will be administered by the intradermal, subcutaneous or intravenous route. A preferred dosage is about 1 μg/kg to about 1 mg/kg, with about 5 μg/kg to about 200 μg/kg particularly preferred. It will be evident to those skilled in the art that the number and frequency of administration will be dependent upon the response of the patient. It may be desirable to administer the HER-2/neu polypeptide repetitively. It will be evident to those skilled in this art that more than one HER-2/neu polypeptide may be administered, either simultaneously or sequentially. Preferred peptides for immunization are those that include the amino acid sequence of SEQ ID NO:2 beginning at about the lysine residue at amino acid position 676 and extending to about the valine residue at amino acid position 1255. It will be appreciated by those in the art that the present invention contemplates the use of an intact HER-2/neu polypeptide as well as division of such a polypeptide into a plurality of peptides. Neither intact $p185^{HER-2/neu}$ protein nor a peptide having the amino acid sequence of its entire extracellular domain (i.e., a peptide having an amino acid sequence of SEQ ID NO:2 from amino acid position 1 up to amino acid position 650, plus or minus about one to five positions, and with or without the first 21 amino acid positions) are used alone for immunization.

A HER-2/neu polypeptide (or nucleic acid) is preferably formulated for use in the above methods as a pharmaceutical composition (e.g., vaccine). Pharmaceutical compositions generally comprise one or more polypeptides in combination with a pharmaceutically acceptable carrier, excipient or diluent. Such carriers will be nontoxic to recipients at the dosages and concentrations employed. The use of a HER-2/neu polypeptide in conjunction with chemotherapeutic agents is also contemplated.

In addition to the HER-2/neu polypeptide (which functions as an antigen), it may be desirable to include other components in the vaccine, such as a vehicle for antigen delivery and immunostimulatory substances designed to enhance the protein's immunogenicity. Examples of vehicles for antigen delivery include aluminum salts, water-in-oil emulsions, biodegradable oil vehicles, oil-in-water emulsions, biodegradable microcapsules, and liposomes. Examples of immunostimulatory substances (adjuvants) include N-acetylmuramyl-L-alanine-D-isoglutamine (MDP), lipopoly-saccharides (LPS), glucan, IL-12, GM-CSF, gamma interferon and IL-15. It will be evident to those of ordinary skill in this art that a HER-2/neu polypeptide for a vaccine may be prepared synthetically or be naturally derived.

While any suitable carrier known to those of ordinary skill in the art may be employed in the pharmaceutical compositions of this invention, the type of carrier will vary depending on the mode of administration and whether a sustained release is desired. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109. A HER-2/neu polypeptide may be encapsulated within the biodegradable microsphere or associated with the surface of the microsphere. For example, in a preferred embodiment, a polypeptide having the amino acid sequence of SEQ ID NO:2 from amino acid 676 through amino acid 1255 is encapsulated within a biodegradable microsphere. In this regard, it is preferable that the microsphere be larger than approximately 25 microns.

Pharmaceutical compositions (including vaccines) may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, product is formulated as a lyophilizate using appropriate excipient solutions (e.g., sucrose) as diluents.

As an alternative to the presentation of HER-2/neu polypeptides, the subject invention includes compositions capable of delivering nucleic acid molecules encoding a HER-2/neu polypeptide. Such compositions include recombinant viral vectors (e.g., retroviruses (see WO 90/07936, WO 91/02805, WO 93/25234, WO 93/25698, and WO 94/03622), adenovirus (see Berkner, *Biotechniques* 6:616627, 1988; Li et al., *Hum. Gene Ther.* 4:403–409, 1993; Vincent et al., *Nat. Genet.* 5:130–134, 1993; and Kolls et al., *Proc. Natl. Acad. Sci. USA* 91:215–219, 1994), pox virus (see U.S. Pat. No. 4,769,330; U.S. Pat. No. 5,017,487; and WO 89/01973)), naked DNA (see WO 90/11092), nucleic acid molecule complexed to a polycationic molecule (see WO 93/03709), and nucleic acid associated with liposomes (see Wang et al., *Proc. Natl. Acad. Sci. USA* 84:7851, 1987). In certain embodiments, the DNA may be linked to killed or inactivated adenovirus (see Curiel et al., *Hum. Gene Ther.* 3:147–154, 1992; Cotton et al., *Proc. Natl. Acad. Sci. USA* 89:6094, 1992). Other suitable compositions include DNA-ligand (see Wu et al., *J. Biol. Chem.* 264:16985–16987, 1989) and lipid-DNA combinations (see Felgner et al., *Proc. Natl. Acad. Sci. USA* 84:7413–7417, 1989). In addition, the efficiency of naked DNA uptake into cells may be increased by coating the DNA onto biodegradable beads.

In addition to direct in vivo procedures, ex vivo procedures may be used in which cells are removed from an animal, modified, and placed into the same or another animal. It will be evident that one can utilize any of the compositions noted above for introduction of HER-2/neu nucleic acid molecules into tissue cells in an ex vivo context. Protocols for viral, physical and chemical methods of uptake are well known in the art.

Accordingly, the present invention is useful for enhancing or eliciting, in a patient or cell culture, a cellular immune response (e.g., the generation of antigen-specific cytolytic T cells). As used herein, the term "patient" refers to any warm-blooded animal, preferably a human. A patient may be afflicted with cancer, such as breast cancer, or may be normal (i.e., free of detectable disease and infection). A "cell culture" is any preparation of T cells or isolated component cells (including, but not limited to, macrophages, monocytes, B cells and dendritic cells). Such cells may be isolated by any of a variety of techniques well known to those of ordinary skill in the art (such as Ficoll-hypaque density centrifugation). The cells may (but need not) have been isolated from a patient afflicted with a HER-2/neu associated malignancy, and may be reintroduced into a patient after treatment.

The present invention also discloses that HER-2/neu polypeptide, in addition to being immunogenic to T cells, appears to stimulate B-cells to produce antibodies capable of recognizing HER-2/neu polypeptide. Antibodies specific (i.e., which exhibit a binding affinity of about 107 liters/mole or better) for HER-2/neu protein may be found in a variety of body fluids including sera and ascites. Briefly, a body fluid sample is isolated from a warm-blooded animal, such as a human, for whom it is desired to determine whether antibodies specific for HER-2/neu polypeptide are present. The body fluid is incubated with HER-2/neu polypeptide under conditions and for a time sufficient to permit immunocomplexes to form between the polypeptide and antibodies specific for the protein. For example, a body fluid and HER-2/neu polypeptide may be incubated at 4° C. for 24–48 hours. Following the incubation, the reaction mixture is tested for the presence of immunocomplexes. Detection of one or more immunocomplexes formed between HER-2/neu polypeptide and antibodies specific for HER-2/neu polypeptide may be accomplished by a variety of known techniques, such as radioimmunoassays (RIA) and enzyme linked immunosorbent assays (ELISA).

Suitable immunoassays include the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods,* E. and S. Livingstone, Edinburgh, 1970); the "western blot" method of Gordon et al. (U.S. Pat. No. 4,452,901); immunoprecipitation of labeled ligand (Brown et al., *J. Biol. Chem.* 255:4980–4983, 1980); enzyme-linked immunosorbent assays as described by, for example, Raines and Ross (*J. Biol. Chem.* 257:5154–5160, 1982); immunocytochemical techniques, including the use of fluorochromes (Brooks et al., *Clin. Exp. Immunol.* 39:477, 1980); and neutralization of activity [Bowen-Pope et al., *Proc. Natl. Acad. Sci. USA* 81:2396–2400 (1984)], all of which are hereby incorporated by reference. In addition to the immunoassays described above, a number of other immunoassays are available, including those described in U.S. Pat. Nos.: 3,817,827; 3,850,752; 3,901,654; 3,935,074; 3,984,533; 3,996,345; 4,034,074; and 4,098,876, all of which are herein incorporated by reference.

For detection purposes, HER-2/neu polypeptide ("antigen") may either be labeled or unlabeled. When unlabeled, the antigen finds use in agglutination assays. In addition, unlabeled antigen can be used in combination with labeled molecules that are reactive with immunocomplexes, or in combination with labeled antibodies (second antibodies) that are reactive with the antibody directed against HER-2/neu polypeptide, such as antibodies specific for immunoglobulin. Alternatively, the antigen can be directly labeled. Where it is labeled, the reporter group can include radioisotopes, fluorophores, enzymes, luminescers, or dye particles. These and other labels are well known in the art and are described, for example, in the following U.S. Pat. No.: 3,766,162; 3,791,932; 3,817,837; 3,996,345; and 4,233,402.

Typically in an ELISA assay, antigen is adsorbed to the surface of a microtiter well. Residual protein-binding sites on the surface are then blocked with an appropriate agent, such as bovine serum albumin (BSA), heat-inactivated normal goat serum (NGS), or BLOTTO (buffered solution of nonfat dry milk which also contains a preservative, salts, and an antifoaming agent). The well is then incubated with a sample suspected of containing specific antibody. The sample can be applied neat, or, more often, it can be diluted, usually in a buffered solution which contains a small amount (0.1%–5.0% by weight) of protein, such as BSA, NGS, or BLOTTO. After incubating for a sufficient length of time to allow specific binding to occur, the well is washed to remove unbound protein and then incubated with an anti-species specific immunoglobulin antibody labeled with a reporter group. The reporter group can be chosen from a variety of enzymes, including horseradish peroxidase, beta-galactosidase, alkaline phosphatase, and glucose oxidase. Sufficient time is allowed for specific binding to occur, then the well is again washed to remove unbound conjugate, and the substrate for the enzyme is added. Color is allowed to develop and the optical density of the contents of the well is determined visually or instrumentally.

In one preferred embodiment of this aspect of the present invention, a reporter group is bound to HER-2/neu protein. The step of detecting immunocomplexes involves removing substantially any unbound HER-2/neu protein and then detecting the presence or absence of the reporter group.

In another preferred embodiment, a reporter group is bound to a second antibody capable of binding to the antibodies specific for HER-2/neu protein. The step of detecting immunocomplexes involves (a) removing substantially any unbound antibody, (b) adding the second antibody, (c) removing substantially any unbound second antibody and then (d) detecting the presence or absence of the reporter group. Where the antibody specific for HER-2/neu protein is derived from a human, the second antibody is an anti-human antibody.

In a third preferred embodiment for detecting immunocomplexes, a reporter group is bound to a molecule capable of binding to the immunocomplexes. The step of detecting involves (a) adding the molecule, (b) removing substantially any unbound molecule, and then (c) detecting the presence or absence of the reporter group. An example of a molecule capable of binding to the immunocomplexes is protein A.

It will be evident to one skilled in the art that a variety of methods for detecting the immunocomplexes may be employed within the present invention. Reporter groups suitable for use in any of the methods include radioisotopes, fluorophores, enzymes, luminescers, and dye particles.

In a related aspect of the present invention, detection of immunocomplexes formed between HER-2/neu polypeptide and antibodies in body fluid which are specific for HER-2/neu polypeptide may be used to monitor the effectiveness of cancer therapy, which involves a HER-2/neu polypeptide, for a malignancy in which the HER-2/neu oncogene is associated. Samples of body fluid taken from an individual prior to and subsequent to initiation of therapy may be analyzed for the immunocomplexes by the methodologies described above. Briefly, the number of immunocomplexes detected in both samples are compared. A substantial change in the number of immunocomplexes in the second sample (post-therapy initiation) relative to the first sample (pre-therapy) reflects successful therapy.

The following examples are offered by way of illustration and not by way of limitation.

EXAMPLES

EXAMPLE 1

EXPRESSION AND PURIFICATION OF RECOMBINANT HUMAN HER-2/NEU POLYPEPTIDE

The human HER-2/neu polypeptide was recovered by the PCR method (e.g., U.S. Pat. Nos. 4,683,195; 4,683,202; 4,800,159) from a plasmid prepared according to Di Fiore et al. (King et al., *Science* 229:974–976, 1985; Di Fiore et al., *Science* 237:178–182, 1987) using oligonucleotide primers that additionally introduced a BssHII restriction site and an enterokinase protease site on the 5' end and an EcoRI site on the 3' end. The primer for the 5'-end was 5'-TCT-GGCGCGCTGGATGACGATGACAAGAAACGACGGC-AGCAGAAGATC-3' (SEQ ID NO:3) while the primer for the 3'-end was 5'-TGAATTCTCGAGTCATTACACTGG-CACGTCCAGACCCAG-3' (SEQ ID NO:4). The resulting 1.8 kb PCR fragment was subcloned into the T-vector from Novagen (Madison, Wis., USA) and the sequence of selected clones was determined on the ABI 373 automated DNA sequencer (Applied Biosystems Inc., Foster City, Calif., USA) using overlapping sequencing primers. PCR fragments with sequence that corresponded to the published DNA sequence for the human HER-2/neu cDNA (SEQ ID NO:1; Coussens et al., *Science* 230:1132, 1985; Yamamoto et al., *Nature* 319:230, 1986)were then connected in the correct reading frame via the BssHII site to a modified *E. coli* thioredoxin reductase. A 6Xhistidine affinity tag employed in Ni-NTA affinity purification of the expressed fusion protein was incorporated into the thioredoxin reductase fusion partner. This cDNA for the trxA-human HER-2/neu polypeptide fusion protein was subcloned into a modified pET expression vector for expression in *E. coli*.

While thioredoxin reductase has been reported to stabilize and solubilize other heterologous proteins expressed in *E. coli*, it did not appear to offer any significant advantage for human HER-2/neu polypeptide expression in *E. coli*. While a significant proportion of the trxA-HER-2/neu polypeptide fusion protein was soluble, a majority was expressed in inclusion bodies. The fusion protein was also subjected to degradation during expression in *E. col*. The presence of the thioredoxin reductase fusion partner may, however, stabilize the protein during purification. The availability of monoclonal antibodies to thioredoxin reductase provides a convenient marker to follow during purification.

For purification of the human HER-2/neu polypeptide with the thioredoxin reductase fusion partner containing the 6XHis affinity tag, the *E. coli* pellet was resuspended with protease inhibitors and lysozyme and sonicated. The inclusion bodies were isolated by centrifugation, and are washed 3X with deoxycholate, the last wash being overnight to remove LPS. The washed inclusion bodies are solubilized in GuHCl for Ni purification. The Ni column was eluted with Imidazole in urea and dialyzed against 10 mM Tris pH8. The recovery of HER-2/neu polypeptide using this protocol was from 80%–95% pure full length protein with the main contaminant being degraded protein. From 500 ml of fermentation, 20 mg were recovered. It was >98% HER-2/neu polypeptide. The techniques used herein are well known to those in the art and have been described, for example, in J. Sambrook et al., *Molecular Cloning: A Laboratory Manual*, 2nd Ed., Cold Spring Harbor Laboratory Press, 1989, Cold Spring Harbor, N.Y., USA.

EXAMPLE 2

DENDRITIC CELLS CAN PRIME HUMAN HER-2/NEU POLYPEPTIDE

A. Generation of DC Cultures From Bone Marrow

DC cultures were generated from CD34+ hematopoietic progenitor cells (HPC). CD34+ cells were purified from bone marrow of normal donors using the cell separation system Ceprate LC Kit (CellPro, Bothell, WA, USA). Purity of recovered CD34+ cells was determined by flow cytometric analysis to be 80% to 95%. CD34+ cells were cultured in serum-free medium (X-VIVO 10, Biowhittaker, Inc., Walkersville, Md., USA) supplemented with L-glutamine (584 $\mu$g/l), penicillin (10 IU/ml), streptomycin (100 $\mu$g/ml), 100 ng/ml human rGM-CSF and 50 ng/ml human rIL-6 (Immunex, Seattle, Wash., USA). After 0 to 17 days of culture time, cells were harvested and used for phenotyping and T cell stimulation assays. GM-CSF alone and in combination with IL-4 or TNF$\alpha$ have been described to induce the in vitro growth of DC. In experiments using KLH and OVA as antigens to prime naive T cells, GM-CSF plus IL-6 consistently gave a comparable total stimulation, but with a lower background and thus a higher stimulation index as compared to GM-CSF plus IL-4 or TNF$\alpha$.

B. T Cell Priming Assay

Figure 2:
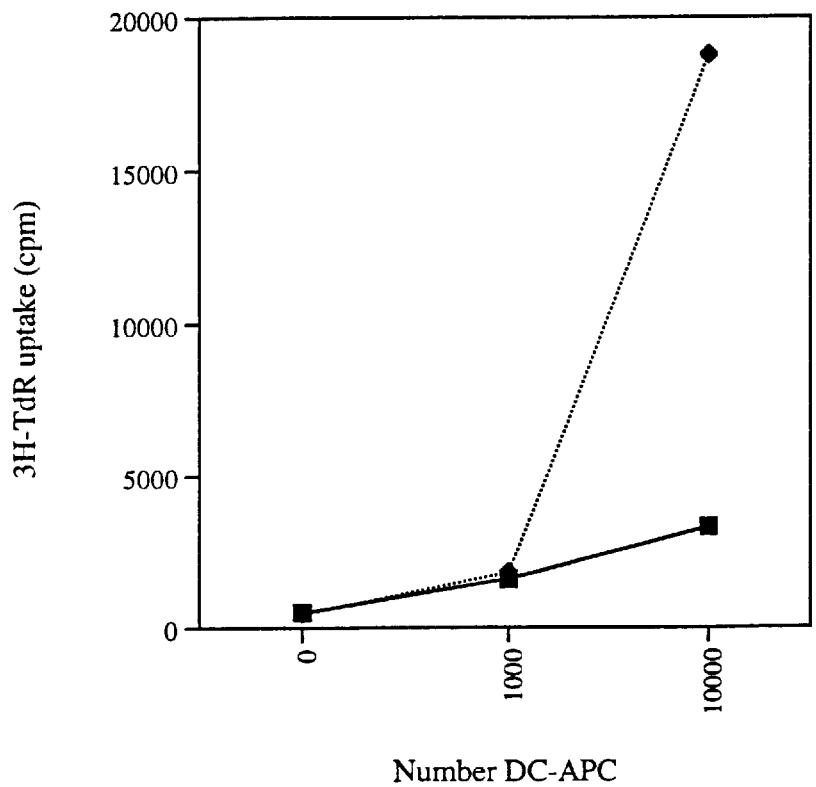
FIG. 2 shows the response of CD4+ cells to HER-2/neu polypeptide. Using the priming assay described for FIG. 1, CD4+ T cells from normal donors were tested for responses to recombinant human HER-2/neu polypeptide. The symbols represent: ■ CD4; and ♦ SC+CD4+HER-2/neu polypeptide. "SC" is stem cells.

Bone marrow derived CD34+ HPC cultured in serum-free medium containing GM-CSF and IL-6 were used as APC after a culture period of 0–17 days. Priming ability of DC was determined by culturing them with autologous, naive T lymphocytes in the presence or absence of the protein antigen recombinant human HER-2/neu polypeptide (hHNP) (10 $\mu$g/ml). CD4+ T lymphocytes were isolated from peripheral blood mononuclear cells by positive selection using immunoaffinity columns (CellPro, Inc., Bothell, Wash., USA). CD4+ CD45RA+ (naive) T lymphocytes were selected from CD4+ T lymphocytes using an anti-CD45RA mAb directly conjugated to FITC (Immunotech, Westbrook, Me., USA) by flow cytometric sorting. The CD4+ CD45RA+ T cells obtained were 99% pure. DC cultures were plated into 96-well round-bottomed plates (Corning, Corning, N.Y., USA) at various concentrations and incubated for 16–18 hours with hHNP 10 $\mu$g/ml final concentration. Antigen-pulsed DC were irradiated (10 Gy), and autologous CD4+ CD45RA+ T lymphocytes were added ($5 \times 10^4$/well). Proliferative response of T cells was measured by the uptake of ($^3$H)thymidine (1 $\mu$Ci/well) added on day 6 for 16–18 hours. Proliferation assays were performed in serum-free and cytokine-free medium. The results are shown in FIG. 1. FIG. 2 shows the results of testing CD4+ T cells, from a normal donor, for responses to hHNP. Similar data was obtained with T cells from nine out of ten normal individuals.

EXAMPLE 3

ASSAY FOR DETECTING Low FREQUENCY LYMPHOCYTE PRECURSORS

Three assays can be used for the detection of CD4+ responses: a standard proliferation assay, a screening method for low frequency events, and a limiting dilution assay (LDA). Conventional proliferative assays are capable of readily detecting primed responses. The proliferative response stimulation index provides a rough correlation with precursor frequency of antigen-reactive T cells. Any specific proliferative response detected from PBL is considered to be a primed response.

To provide a more quantitative interpretation of CD4+ T cell responses, the assay system developed for detecting low lymphocyte precursor frequency responses (described below) is used. This assay is simple and cost-effective. In circumstances in which more precision is needed, the precursor frequency is validated by limiting dilution assays (Bishop and Orosz, *Transplantation* 47:671–677, 1989).

Responses greater than detected in normal individuals are defined as a primed response and imply existent immunity. Low responses, detectable only by LDA conditions are considered to be unprimed responses. An absent response by LDA or a response lower than that defined by the normal population analysis is considered to be tolerance/anergy.

In general, primed CD4$^+$ T cell responses can be detected in conventional proliferative assays, whereas unprimed responses are not detectable in the same assays. Detection of small numbers of unprimed T cells is limited by confounding background thymidine uptake including the autologous mixed lymphocyte response (AMLR) to self MHC antigen plus responses to processed self serum proteins and exogenously added serum proteins.

To elicit and detect unprimed T cells, an assay system for low frequency responses based on Poisson sampling statistics was used (In: *Pinnacles*, Chiron Corporation, 1:1–2, 1991). This type of analysis applies specifically to low frequency events in that, if the precursor frequency is less than the number of cells in one replicate culture, many replicates are required to detect a statistically significant number of positives. Theoretically, the analysis will correct for autologous responses by setting up a known positive control (such as PHA or tetanus toxoid) and known negative control (no antigen) and evaluating all data points from lowest to highest irrespective of the experimental group to which they belong. A cutoff value is calculated based on the equation cutoff=M+(F+SD), where M=arithmetic mean, F=3.29, a factor from tables of standardized normal distribution chosen so not more than 0.1% of the "true negatives" of a normally distributed background will be above the cutoff, and SD =standard deviation. In this screening assay, wells above the cutoff are considered true positives that potentially contain a lymphocyte that is specifically proliferating to the antigen of interest. Although estimations of lymphocyte precursor frequency is possible using this method, precise determination requires formal LDA analysis.

EXAMPLE 4

HER-2/NEU POLYPEPTIDE BASED VACCINE ELICITS IMMUNITY TO HER-2/NEU PROTEIN

A. Animals

Rats used in this study were Fischer strain 344 (CDF (F-344)/CrlBR) (Charles River Laboratories, Portage Mich.). Animals were maintained at the University of Washington Animal facilities under specific pathogen free conditions and routinely used for experimental studies between 3 and 4 months of age.

B. Immunization

Fischer rats were immunized with recombinant rat HER-2/neu polypeptide (rHNP) in a variety of adjuvants (MPL, Vaccel; Ribi, Bozeman, Mont., USA). Animals received 50 $\mu$g of rHNP mixed with adjuvant subcutaneously. Twenty days later the animals were boosted with a second immunization of 50 $\mu$g of rHNP administered in the same fashion. Twenty days after the booster immunization animals were tested for the presence of antibodies directed against rat HER-2/neu protein (neu).

C. Cell Lines

Two cell lines were used as a source of neu proteins. SKBR3, a human breast cancer cell line that is a marked overexpressor of HER-2/neu (American Type Culture Collection, Rockville, Md.), was maintained in culture in 10% fetal bovine serum (FBS) (Gemini Bioproducts, Inc., Calabasas, Calif.) and RPMI. DHFR-G8, an NIH/3T3 cell line cotransfected with cneu-p and pSV2-DHFR (American Type Culture Collection, Rockville, Md.), was used as a source of non-transforming rat neu protein (Bernards et al., *Proc. Natl. Acad. Sci. USA* 84:6854–6858, 1987). This cell line was maintained in 10% FBS and Dulbecco's modified Eagle's medium with 4.5 g/L glucose. DHFR-G8 cells were passaged through the same medium supplemented with 0.3 $\mu$M methotrexate at every third passage to maintain the neu transfectant.

D. Preparation of Cell Lysates

Lysates of both SKBR3 and DHFR-G8 were prepared and used as a source of neu protein. Briefly, a lysis buffer consisting of tris base, sodium chloride and Triton-X (1%) pH 7.5 was prepared. Protease inhibitors were added; aprotinin (1 $\mu$g/ml), benzamidine (1 mM) and PMSF (1 mM). 1 ml of the lysis buffer was used to suspend 10$^7$ cells. The cells were vortexed for 15 seconds every 10 minutes for an hour until disrupted. All procedures were performed on ice in a 4° C. cold room. After disruption the cells were microfuged at 4° C. for 20 minutes. Supernatant was removed from cell debris and stored in small aliquots at −70° C. until used. Presence of human and rat neu in the lysates was documented by Western blot analysis.

Figure 3:
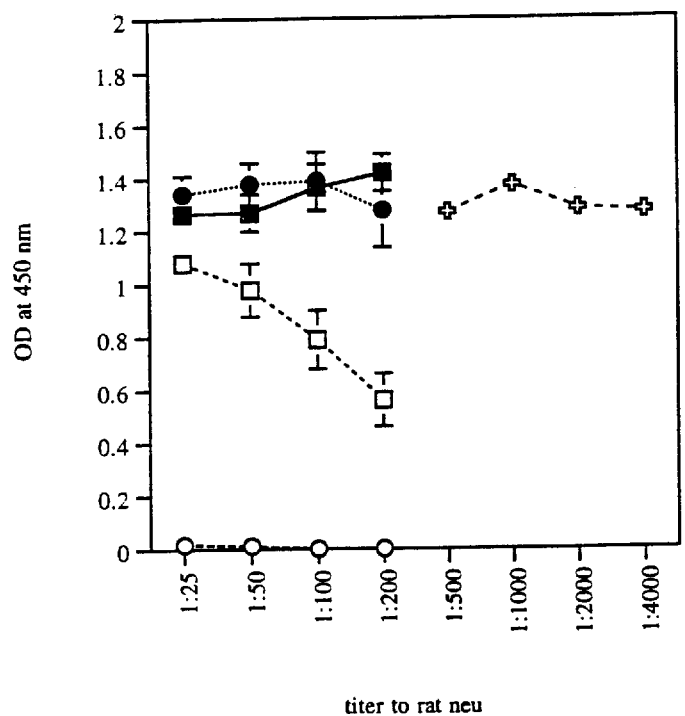
FIG. 3 shows that rats immunized with rat HER-2/neu polypeptide develop rat neu specific antibodies. Rats were immunized with recombinant rat HER-2/neu polypeptide 25 ug in MPL or vaccel adjuvant. Three immunizations were given, each 20 days apart. Twenty days after the final immunization rats were assessed for antibody responses to rat neu. Animals immunized with rat HER-2/neu polypeptide and the vaccel adjuvant showed high titer rat neu specific responses. The control was an animal immunized with human HER-2/neu polypeptide (foreign protein). In separate experiments, rats immunized with 100 ug and 300 ug of purified whole rat neu did not develop detectable neu specific antibodies (data not shown). Data represents the mean and standard deviation of 3 animals. The symbols represent: ■ rat HER-2/neu polypeptide/MPL; ● rat HER-2/neu polypeptide/vaccel; □ MPL alone; ○ vaccel alone; and + control. "MPL" and "vaccel" are adjuvants (Ribi, Bozeman, Mont., USA) "Neu" is HER-2/neu protein.

E. ELISA for Rat neu Antibody Responses 96 well Immulon 4 plates (Baxter SP, Redmond, Wash.: Dynatech Laboratories) were incubated overnight at 4° C. with a rat neu specific monoclonal antibody (Oncogene Science), 7.16.4, at a concentration of 10 $\mu$g/ml diluted in carbonate buffer (equimolar concentrations of Na$_2$CO$_3$ and NaHCO$_3$ pH 9.6). After incubation, all wells were blocked with PBS-1% BSA (Sigma Chemical, St. Louis, Mo., USA), 100 $\mu$l/well for 3 hours at room temperature. The plate was washed with PBS-0.5% Tween and lysates of DHFRG8, a murine cell line transfected with rat neu DNA (American Type Culture Collection, Rockville, Md., USA); a source of rat neu protein, were added to alternating rows. The plate was incubated overnight at 4° C. The plate was then washed with PBS-0.5% Tween and experimental sera was added at the following dilutions: 1:25 to 1:200. The sera was diluted in PBS-1% BSA-1% FBS-25 $\mu$g/ml mouse IgG-0.01% NaN$_3$ and then serially into PBS-1% BSA. 50 $\mu$l of diluted sera was added/well and incubated 1 hour at room temperature. Each experimental sera was added to a well with rat neu and a well without rat neu. Sheep anti-rat Ig F(ab')$_2$ horseradish peroxidase (HRP) was added to the wells at a 1:5000 dilution in PBS-1% BSA and incubated for 45 minutes at room temperature (Amersham Co., Arlington Heights, Ill., USA). Following the final wash, TMB (Kirkegaard and Perry Laboratories, Gaithersburg, Md.) developing reagent was added. Color reaction was read at an optical density of 450 nm. The OD of each serum dilution was calculated as the OD of the rat neu coated wells minus the OD of the PBS-1% BSA coated wells. Sera from animals immunized with the adjuvants alone and an animal immunized with hHNP (foreign protein) were also evaluated in a similar manner. The results are shown in FIG. 3.

F. T Cell Proliferation Assays

For analysis of HER-2/neu polypeptide specific responses: Fresh spleen or lymph node cells are harvested by mechanical disruption and passage through wire mesh and washed. 2×10$^5$ spleen cells/well and 1×10$^5$ lymph node cells/well are plated into 96-well round bottom microtiter plates (Corning, Corning, N.Y.) with 6 replicates per experimental group. The media consists of EHAA 120 (Biofluids) with L-glutamine, penicillin/streptomycin, 2-mercaptoethanol, and 5% FBS. Cells are incubated with polypeptides. After 4 days, wells are pulsed with 1 µCi of [$^3$H]thymidine for 6–8 hours and counted. Data is expressed as a stimulation index (SI) which is defined as the mean of the experimental wells divided by the mean of the control wells (no antigen). For analysis of HER-2/neu protein specific responses: Spleen or lymph node cells are cultured for 3 in vitro stimulations. At the time of analysis 1×10$^5$ cultured spleen or lymph node T cells are plated into 96 well microtiter plates as described above. Cells are incubated with lug/ml immunoaffinity column purified rat neu (from DHFR-G8 cells as the source of rat neu). After 4 days, wells were pulsed with 1 µCi of [$^3$H]thymidine for 6–8 hours and counted. Data is expressed as a stimulation index which is defined as the mean of the experimental wells divided by the mean of the control wells (no antigen).

EXAMPLE 5

PRIMED RESPONSES TO HUMAN HER-2/NEU POLYPEPTIDE CAN BE DETECTED IN PATIENTS WITH BREAST CANCER

Figure 4:
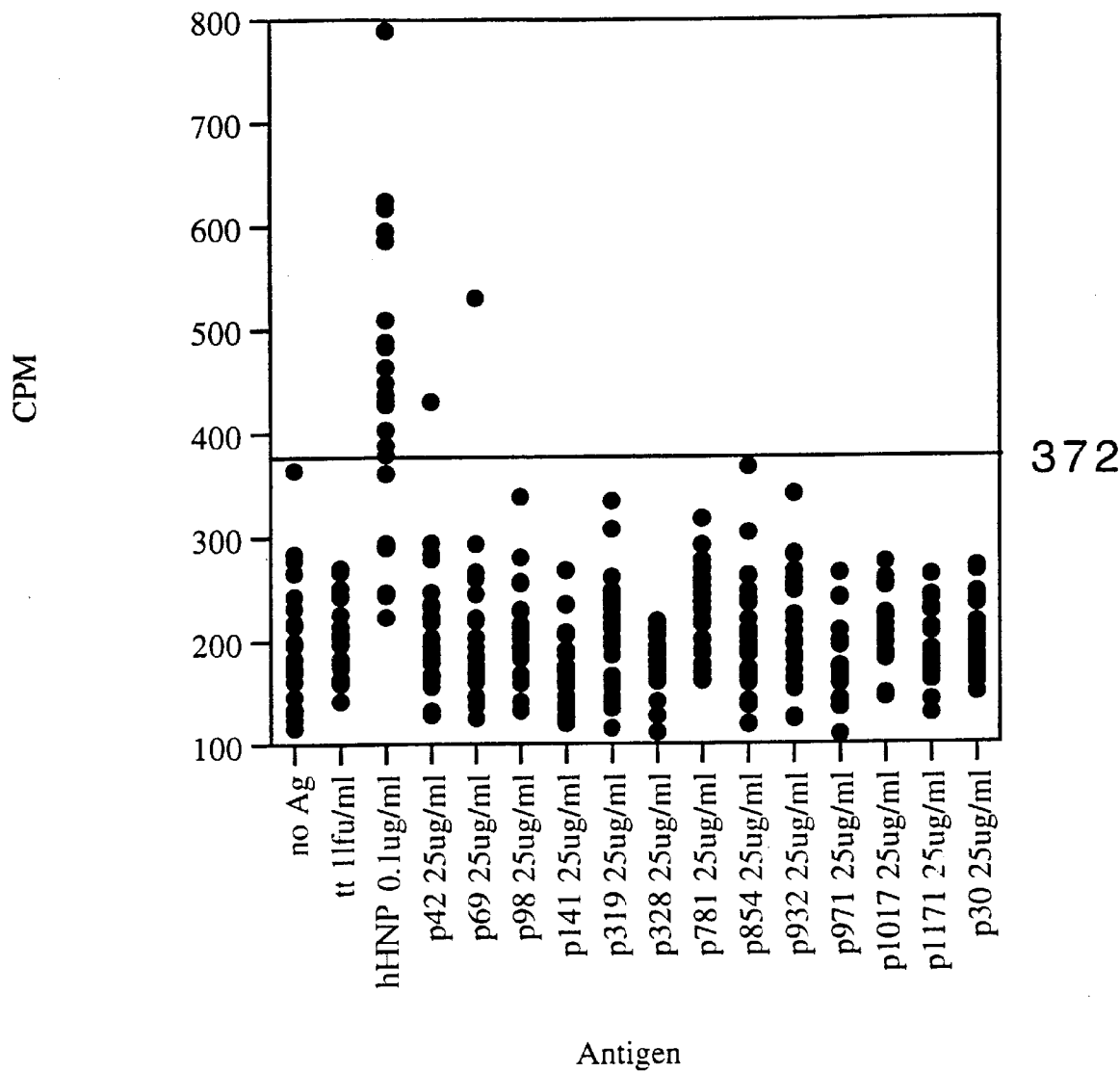
FIG. 4 shows that breast cancer patients have reexistent immunity to HER-2/neu polypeptide. Patient PBMC were evaluated by tritiated thymidine incorporation in 24 well replicates. Responsive wells are scored as greater than the mean and 3 standard deviations (372 cpm) of the control wells. This HER-2/neu positive-stage II breast cancer patient has a significant response to recombinant human HER-2/neu polypeptide. The symbols "p" represent peptides for HER-2/neu protein, "tt" represents tetanus toxoid, and "hHNP" represents recombinant human HER-2/neu polypeptide.

Heparinized blood was obtained from a patient with stage II HER-2/neu overexpressing breast cancer. Peripheral blood mononuclear cells (PBMC) were separated by Ficoll Hypaque density centrifugation. PBMC were plated at a concentration of 2×10$^5$/well in to 96-well round-bottomed plates (Corning, Corning, N.Y., USA). 24 well replicates were performed for each experimental group. Antigens consisting of HER-2/neu derived peptides (15–20 amino acids in length with number of first amino acid in sequence listed) 25 µg/m human HER-2/neu polypeptide (hHNP) 1 µg/ml, tetanus toxoid 1 µg/ml, and p30 a peptide derived from tetanus 25 µg/ml were added to each 24 well replicate. The assay was performed in media containing 10% human sera. Proliferative response of T cells was measured by the uptake of ($^3$H) thymidine (1 µCi/well) added on day 4 for 10 hours. Positive wells, antigen reactive wells, were scored as positive if the cpm was greater than the mean and 3 standard deviations of the no antigen wells. The results are shown in FIG. 4. This stage II breast cancer patient has a significant response to recombinant hHNP.

All publications and patent applications mentioned in this specification are herein incorporated by reference to the same extent as if each individual publication or patent application was specifically and individually incorporated by reference.

From the foregoing, it will be evident that, although specific embodiments of the invention have been described herein for purposes of illustration, various modifications may be made without deviating from the spirit and scope of the invention.

We claim:

1. A method for eliciting or enhancing an immune response to HER-2/neu protein, comprising administering to a human in an amount effective to elicit or enhance said response a polypeptide encoded by a DNA sequence selected from:

(a) nucleotides 2026 through 3765 of SEQ ID NO: 1; and (b) DNA sequences that hybridize to a nucleotide sequence complementary to nucleotides 2026 through 3765 of SEQ ID NO:1 under moderately stringent conditions, wherein the DNA sequence encodes a polypeptide that produces an immune response to HER-2/neu protein, and wherein the hybridization conditions comprise prewashing in a solution of 5×SSC, 0.5% SDS 1.0 mM EDTA (pH 8.0); hybridizing at 50° C.–65° C. 5×SSC, overnight: followed by washing twice at 65° C. for 20 minutes with each of 2X, 0.5X and 0.2X SSC, containing 0.1% SDS.

2. The method of claim 1 wherein the polypeptide has the amino acid sequence of SEQ ID NO:2 from lysine, amino acid 676, through valine, amino acid 1255, or a conjugate thereof with a peptide or polypeptide having immunogenic properties.

3. The method of claim 2 wherein the polypeptide has the amino acid sequence of SEQ ID NO:2 from amino acid 676 through amino acid 1255.

4. The method of claim 1 wherein the polypeptide is in combination with a pharmaceutically acceptable carrier or diluent.

* * * * *